United States Patent
Peyser et al.

(10) Patent No.: US 8,972,196 B2
(45) Date of Patent: *Mar. 3, 2015

(54) ALGORITHMS FOR CALIBRATING AN ANALYTE SENSOR

(75) Inventors: Thomas A. Peyser, Menlo Park, CA (US); Soya Gamsey, Huntington Beach, CA (US); Matthew A. Romey, Newport Beach, CA (US); David R. Markle, Berwyn, PA (US)

(73) Assignee: Medtronic Minimed, Inc., Northridge, CA (US)

( * ) Notice: Subject to any disclaimer, the term of this patent is extended or adjusted under 35 U.S.C. 154(b) by 629 days.

This patent is subject to a terminal disclaimer.

(21) Appl. No.: 12/794,466

(22) Filed: Jun. 4, 2010

(65) Prior Publication Data

US 2010/0312483 A1    Dec. 9, 2010

Related U.S. Application Data

(60) Provisional application No. 61/184,747, filed on Jun. 5, 2009.

(51) Int. Cl.
| | | |
|---|---|---|
| *G06F 17/11* | (2006.01) | |
| *G06F 17/50* | (2006.01) | |
| *G01N 33/52* | (2006.01) | |
| *G01N 33/66* | (2006.01) | |
| *G01N 31/22* | (2006.01) | |

(52) U.S. Cl.
CPC ............... *G01N 33/52* (2013.01); *G01N 33/66* (2013.01); *G01N 31/22* (2013.01)
USPC ................ 702/19; 702/23; 600/345; 600/347

(58) Field of Classification Search
CPC ......... G01N 33/50; G06F 19/10; G06F 19/36; G06F 19/366
See application file for complete search history.

(56) References Cited

U.S. PATENT DOCUMENTS

| | | | |
|---|---|---|---|
| 4,810,655 A | 3/1989 | Khalil et al. | |
| 5,156,962 A | 10/1992 | Suzuki et al. | |
| 5,810,985 A | 9/1998 | Boa et al. | |
| 6,602,702 B1 | 8/2003 | McDevitt et al. | |
| 7,276,029 B2 | 10/2007 | Goode, Jr. et al. | |
| 2005/0130249 A1 | 6/2005 | Parris et al. | |
| 2006/0189863 A1 | 8/2006 | Peyser et al. | |
| 2008/0187655 A1 | 8/2008 | Markle et al. | |
| 2008/0296155 A1 | 12/2008 | Shults et al. | |
| 2009/0005266 A1 | 1/2009 | Ostermeir et al. | |
| 2009/0082566 A1 | 3/2009 | Mitra | |
| 2009/0088329 A1 | 4/2009 | Brennan et al. | |
| 2009/0098052 A1 | 4/2009 | Schilling et al. | |
| 2011/0224516 A1 | 9/2011 | Romey et al. | |

FOREIGN PATENT DOCUMENTS

WO    WO 2010/141888    9/2010

OTHER PUBLICATIONS

Ballerstadt et al. Anal. Chem. 2000, 72, 4185-4192.*
Xiao et al. Biophys. J. 95, 1382-1392, 2008.*
Badugu et al. Journal of Fluorescence, 14 (5), 617-633, 2004.*
PCT International Search Report and Written Opinion in App. No. PCT/US2011/028222, dated May 6, 2011, in 30 pages.
PCT International Search Report and Written Opinion re PCT/US2010/037502, dated Aug. 6, 2010.
Stokes, et al.: "An optical oxygen sensor and reaction vessel for high-pressure applications", Limnol. Oceanogr., 44(1), 1999, 189-195.
"Fiber Optic Oxygen Sensors: Theory of Operation", Fiber Optic Oxygen Sensors Theory of Operation, http://www.oceanoptics.com/Products/sensortheory.asp—4 pages.
PCT International Search Report re PCT/US2010/037502 dated Aug. 6, 2010.
PCT International Preliminary Report on Patentability re PCT/US2010/037502, dated Dec. 6, 2011.

* cited by examiner

*Primary Examiner* — Michael Borin
(74) *Attorney, Agent, or Firm* — Medtronic Minimed, Inc.

(57) ABSTRACT

Disclosed are embodiments that relate to algorithms and methods for calibrating an analyte sensor, and more particularly, to algorithms for calibrating an optical glucose sensor comprising an equilibrium fluorescent chemical indicator system. In particular, a method of detecting an analyte concentration is disclosed where a modified Michaelis-Menten equation comprising Michaelis-Menten parameters is used to characterize the signal generated by the analyte sensor.

10 Claims, 23 Drawing Sheets

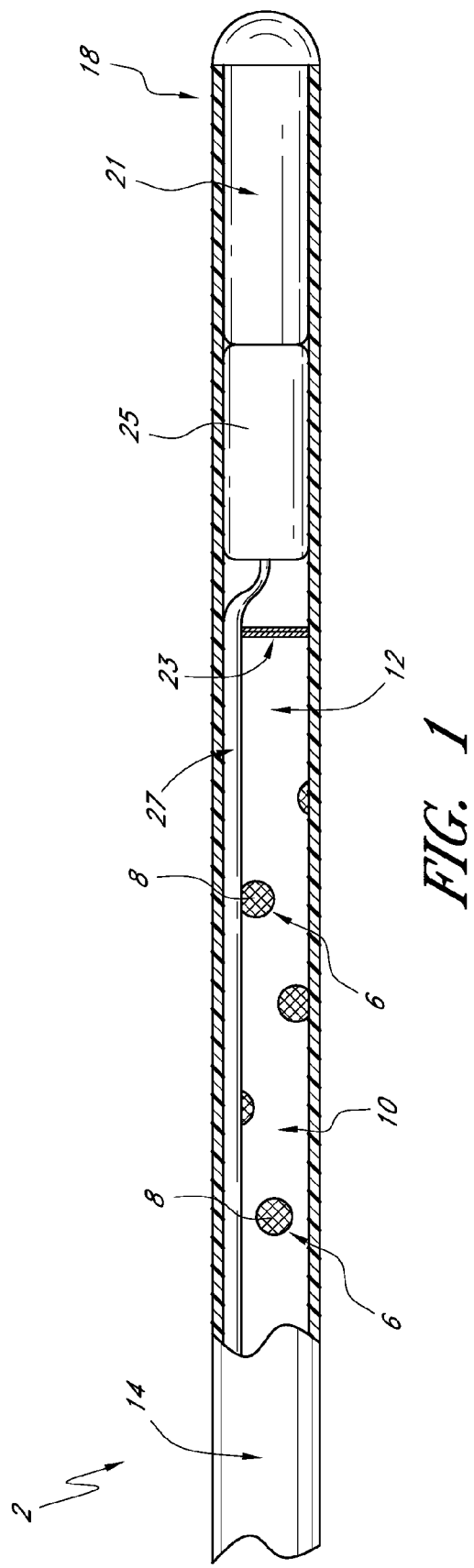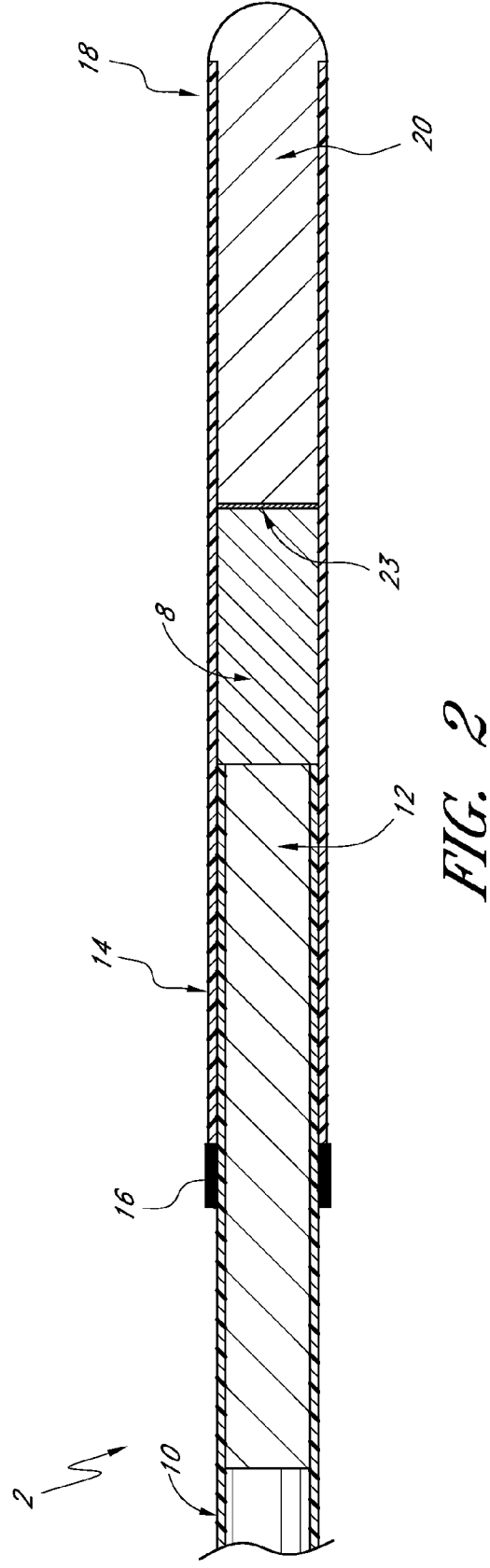

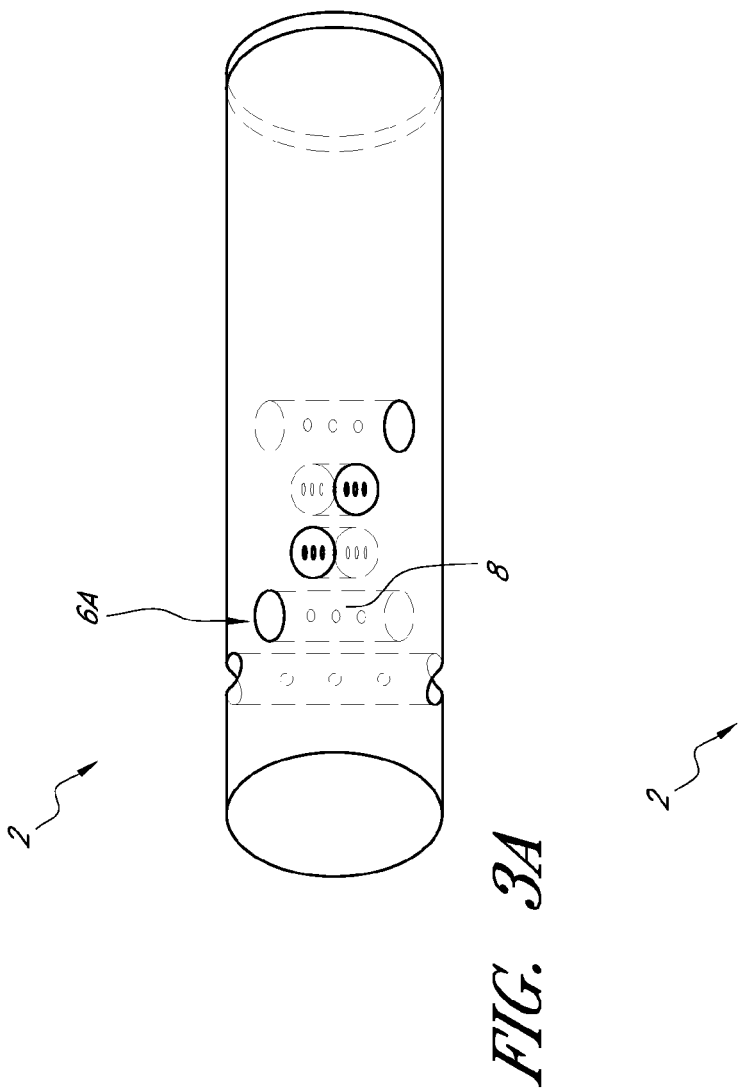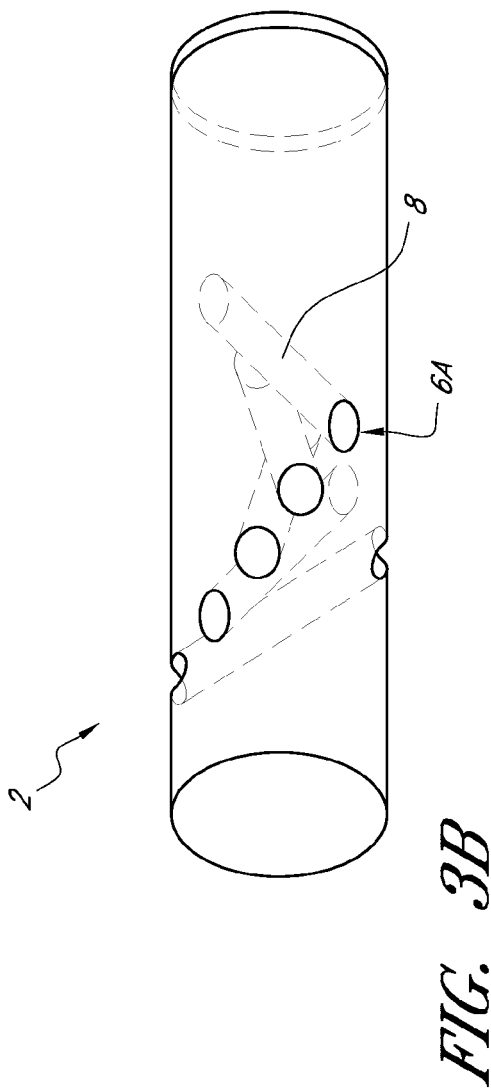
FIG. 3A
FIG. 3B

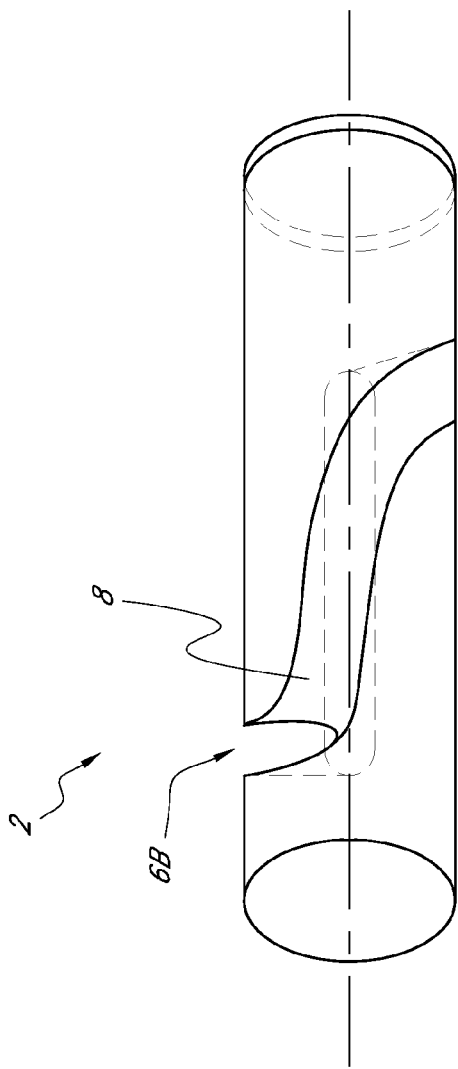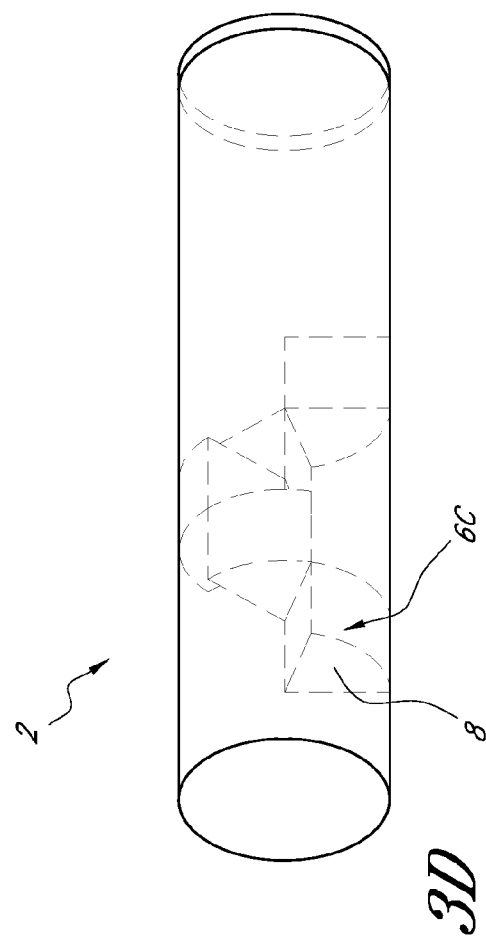
FIG. 3C
FIG. 3D

* Dimension Clinical Chemistry System, model RxL, Dade Behring, Inc., Deerfield, Ill.
Lacara, T. et al."Comparison of Point-of-care and laboratory glucose analysis in critically ill patients" Am J. Crit Care, 16, 336-347, 2007)

ALGORITHMS FOR CALIBRATING AN ANALYTE SENSOR

CROSS-REFERENCE TO RELATED APPLICATIONS

This application claims priority to U.S. Provisional Patent Application No. 61/184,747, filed Jun. 5, 2009 the disclosure of which is hereby expressly incorporated by reference and hereby expressly made a portion of this application. This application is also related to U.S. patent application Ser. No. 11/671,880, filed Feb. 6, 2007, Ser. No. 11/782,553, filed Jul. 24, 2007, Ser. No. 12/118,429, filed May 9, 2008, Ser. No. 12/113,876, filed May 1, 2008, Ser. No. 12/172,059, filed Jul. 11, 2008, Ser. No. 12/027,158, filed Feb. 6, 2008, Ser. No. 12/187,248, filed Aug. 6, 2008, Ser. No. 12/118,401, filed May 9, 2008, and Ser. No. 12/274,617, filed Nov. 20, 2008, the disclosure of each of which are hereby expressly incorporated by reference in their entireties and are hereby expressly made a portion of this application.

BACKGROUND OF THE INVENTION

1. Field of the Invention

Disclosed herein are algorithms and methods for calibrating an analyte sensor, and more particularly, algorithms and methods for calibrating an optical glucose sensor comprising a fluorophore operably coupled to a glucose binding moiety.

2. Description of the Related Art

Analyte sensors, such as glucose sensors, for detecting and measuring the presence of different chemical species, such as glucose, in samples are well known. To assure analyte measurement accuracy, whether as a gauge of the amount of analyte present or to agree with a measurement made by another instrument, an analyte sensor generally requires calibration. Such calibration is frequently necessary to account for sensor-to-sensor variation and for differences in the environment where the sensor will be placed. Such calibration can be difficult and time-consuming, and may be prone to errors.

In addition, calibration of some sensors, such as some that detect glucose concentration in the blood stream, are frequently calibrated after placement in the bloodstream. Such calibration can be time-consuming, uncomfortable, and intrusive for a patient, requiring multiple blood draws or constant sampling for ex-vivo analysis of blood sugar concentration to compare to a signal comprising the output of the analyte sensor. In cases where the sensor output is not linear when compared to the concentration of analyte, or only linear for a range of concentrations, additional complexity and potential uncertainty can be involved requiring greater attention, more time, and more difficulty in performing a reliable calibration.

In addition, analyte measurements of the same sample taken by different methodologies can in some instances result in different concentrations of analyte being reported. These differences in concentrations reported for the same sample may be due to differences in the analytical technique, differences in sample preparation, or for other reasons as well. For example, some analyte measurement techniques dilute a sample of blood prior to determining the analyte level in solution, while other techniques simply determine the analyte level on a non-diluted sample of blood. In some instances, such dilution can result in additional analyte being extracted from cells present in the blood sample, resulting in a change in the amount of analyte that would be reported by the different methods. Other changes in technique can also result in shifts in reported values, such as when samples are filtered or centrifuged as a part of the procedure, or when a sensor based on a different technology is used. In some instances, problems can occur when measurements for a patient are made by one methodology, and the treatment protocol had been determined based on another methodology.

Errors in calibration of analyte sensors can lead to erroneous measurements. Reliance on such erroneous measurements, such as for medical treatment, or a mismatch between analytical technique and treatment protocol can lead to adverse responses and possibly life-threatening situations. As a result, there is a need for improved methods for calibration of analyte sensors and for correcting readings to agree with other measurement techniques.

SUMMARY OF THE INVENTION

Disclosed herein are methods for calibrating analyte sensors. In some embodiments, the methods include the use of a modified version of the Michaelis-Menten equation. In certain such embodiments, the methods include determining the values of a set of Michaelis-Menten parameters. In certain embodiments, the methods include determining a correction factor through the use of a one-point in vivo calibration. In certain embodiments, the methods include determining a correction factor through the use of a one-point in vitro calibration. In certain embodiments, determining the values of the Michaelis-Menten parameters and/or a correction factor includes the use of calibration solutions of known analyte concentration. In certain such embodiments, the parameters and/or correction factor are used to estimate an analyte concentration from an optical intensity. In some embodiments, the methods are used to calibrate a sensor employing a fluorophore and analyte binding moiety, and in some instances, the sensor may further employ an immobilizing matrix. In some embodiments, the methods are used to calibrate a glucose sensor, and in certain such embodiments, the glucose sensor is included in a system configured to achieve glycemic control over a patient's blood glucose concentration.

A method is disclosed in one preferred embodiment for determining an analyte concentration in a solution or suspension. The method comprises: providing a sensor comprising a chemical indicator system adapted to generate a signal related to the analyte concentration in the solution or suspension; contacting the chemical indicator system with the solution or suspension, thereby generating the signal; and determining the analyte concentration from the signal using a modified Michaelis-Menten equation comprising Michaelis-Menten parameters.

In a variation to the method, the Michaelis-Menten parameters are determined from a set of ex vivo measurements of the signal using one or more solutions of known analyte concentrations. The Michaelis-Menten parameters may be determined during a factory calibration of the chemical indicator system.

The method may also comprise an ex vivo calibration with one or more solutions of known analyte concentration to determine a correction factor. In one preferred variation, the ex vivo calibration comprises: measuring the signal with 100 mg/dL of analyte at 42° C. for 90 minutes; and measuring the signal with 100 mg/dL of analyte at 33° C. for 120 minutes. In another variation, the ex vivo calibration comprises: measuring the signal with 0 mg/dL of analyte; measuring the signal with 100 mg/dL of analyte; and measuring the signal with 400 mg/dL of analyte. The method may also comprise an in vivo or in vitro calibration with an independent analyte measurement.

In one embodiment, the method may also include: measuring the signal after placement of the chemical indicator system in an in vitro or in vivo environment; measuring the analyte concentration independent of the chemical indicator system; calculating a correction factor by comparing the measured signal with a predicted signal calculated by the analyte concentration measured independently of the chemical indicator system; and correcting the Michaelis-Menten parameters with the correction factor.

In one embodiment, the modified Michaelis-Menten equation is:

$$[X] = c*(I-a)/(a+b-1), \text{ wherein}$$

[X] is the analyte concentration
I is the signal intensity
a is the signal intensity in the absence of analyte
b is the asymptotic signal intensity at infinite analyte concentration, minus (a), and
c is the analyte concentration at which the signal intensity is one-half the difference between (b) and (a).

In a preferred embodiment of the disclosed method, the analyte is glucose, the chemical indicator system comprises a equilibrium fluorescence chemical indicator, the signal is a fluorescent signal, and the modified Michaelis-Menten equation is:

$$F = F_{min} + F_{max} K[X]/(1+K[X]), \text{ wherein}$$

[X] is the glucose concentration,
F is the fluorescent signal intensity,
$F_{min}$ is the fluorescent signal intensity in the absence of glucose,
$F_{max}$ is the maximum fluorescent signal intensity when the system is saturated with glucose, and
K is the binding affinity of the equilibrium fluorescence chemical indicator for glucose.

A measurement device for estimating an analyte concentration of a sample is disclosed in accordance with another embodiment. The measurement device comprises: an analyte sensing element comprising a chemical indicator system configured to generate a signal indicative of the analyte concentration; and a processing module configured to transform the signal utilizing an equation of the form of a modified Michaelis-Menten equation depending on Michaelis-Menten parameters, wherein values of the Michaelis-Menten parameters are set based upon calibration data.

The measurement device may also include a calibration system configured to perform an ex vivo calibration. The calibration system may comprise: one or more solutions with known analyte concentrations; and a temperature controlling module configured to control the temperature of the one or more solutions with known analyte concentrations.

The processing module of the measurement device is preferably configured to correct the Michaelis-Menten parameters by multiplying said parameters by a correction factor calculated by comparing the in vitro or in vivo measured signal with a predicted signal calculated by the analyte concentration measured independently of the measurement device.

The modified Michaelis-Menten equation used by the processing module is characterized by the equation:

$$[X] = c*(I-a)/(a+b-1), \text{ wherein}$$

[X] is the analyte concentration
I is the signal intensity
a is the signal intensity in the absence of the analyte
b is the asymptotic signal intensity at infinite analyte concentration, minus the signal intensity in the absence of analyte (a), and
c is the analyte concentration at which the signal intensity is one-half the difference between the asymptotic value (b) and the background (a).

In a preferred embodiment of the measurement device, the analyte is glucose, the chemical indicator system comprises a fluorophore operably coupled to a glucose binding moiety, the signal is a fluorescent signal, and the modified Michaelis-Menten equation is:

$$F = F_{min} + F_{max} K[X]/(1+K[X]), \text{ wherein}$$

[X] is the glucose concentration,
F is the fluorescent signal intensity,
$F_{min}$ is the fluorescent signal intensity in the absence of glucose,
$F_{max}$ is the maximum fluorescent signal intensity when the system is saturated with glucose, and
K is the binding affinity of the glucose binding moiety of the chemical indicator system.

BRIEF DESCRIPTION OF THE DRAWINGS

FIG. 1 is a cut-away view of a sensor where a portion of the porous membrane sheath is cut away to expose the optical fiber and hydrogel beneath the membrane.

FIG. 2 is a cross-sectional view along a longitudinal axis of a sensor with a hydrogel disposed distal to the optical fiber.

FIG. 3A shows a glucose sensor having a series of holes that form a helical configuration.

FIG. 3B shows a glucose sensor having a series of holes drilled or formed at an angle.

FIG. 3C shows a glucose sensor having at least one spiral groove.

FIG. 3D shows a glucose sensor having a series of triangular wedge cut-outs.

DETAILED DESCRIPTION OF THE PREFERRED EMBODIMENT

Figure 4:
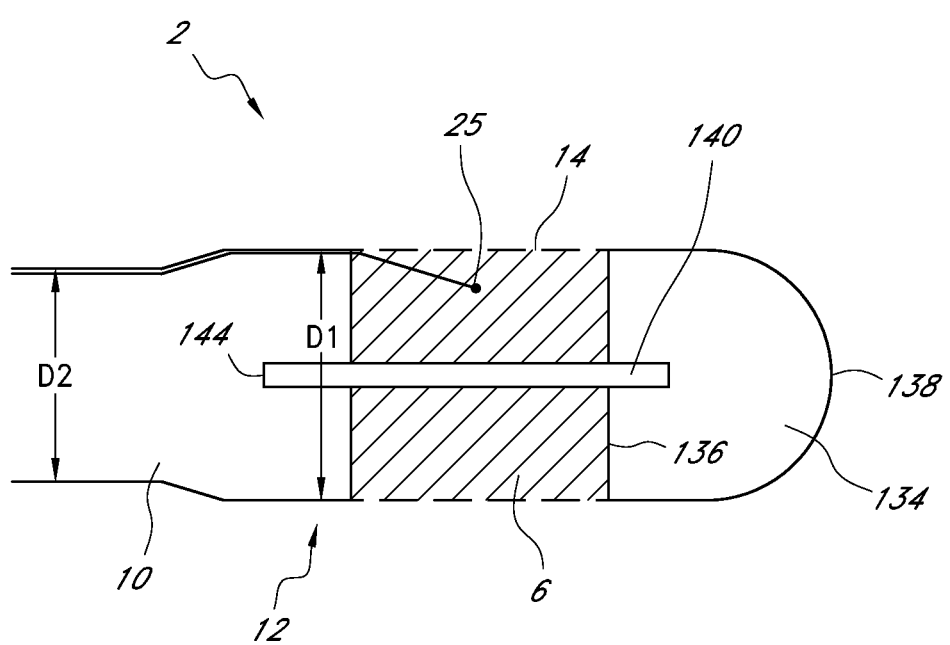
FIG. 4 shows a cross-sectional view of one embodiment of a glucose sensor having a cavity in the distal portion of the sensor.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Disclosed herein are methods of calibrating an analyte sensor capable of measuring the concentration of an analyte. The methods of calibrating can be used on various systems that are configured to measure the concentration of an analyte, such as a fluorescent based system, lifetime chemistry based system, electrochemical system, and other systems known in the art. In various embodiments, the calibration can be used with the sensor to determine the amount of analyte present, or the amount that another method or instrument would determine to be present, and in some embodiments to display the analyte concentration on a computer screen, display the analyte concentration on an instrument screen, record the analyte concentration on paper or computer readable medium, transmit the concentration to another device, or determine an amount of medication to deliver and to deliver the medication to the patient. In some embodiments, the calibration methods are used for calibrating a glucose sensor which in turn is used in conjunction with a glucose delivery device to achieve tight glycemic control over a patient's blood glucose level. In some preferred embodiments, the method of calibration can be used to relate readings made by a sensor being calibrated to readings made by another method, technique, or sensor which is sufficiently linear, or linearizable to provide acceptable agreement over a range of analyte concentrations of interest.

In some embodiments, the methods disclosed herein can be used to calibrate an optical sensor wherein a light-sensitive compound having or being bound to or functionally interacting with an analyte binding moiety which modifies the emitted, absorbed, or reflected spectrum or intensity of light in a reproducible and reversible fashion in response to changes in the amount of analyte bound to the binding moiety. In some embodiments, the amount of emitted light can increase or decrease, or a different wavelength can be detected after incident light interacts with the sensor, such as is described in U.S. Pat. Nos. 5,137,833, 5,512,246, 5,503,770, 6,304,766, 6,766,183, and 6,804,544, and U.S. patent application Ser. Nos. 11/671,880, 12/027,158, 11/671,880, 12/027,158, 12/172,059, 12/118,401, and 11/782,553, incorporated by reference herein in their entireties.

In some embodiments, a functionalized dye can be used which can include a boronic acid or arsenious acid or germanic acid group. In some embodiments, a fluorescent dye can be combined with an amine nitrogen quenching functionality and derivatized boronic, germanic, or arsenious acid in a single complex. In some embodiments, a derivatized boronic, germanic, or arsenious acid can be capable of binding to an analyte of interest. Particular analytes of interest can include those having multiple hydroxyl groups especially vicinal hydroxyl groups and can be carbohydrates such as simple sugars (for example, glucose). Preferred derivatives of boronic, germanic, or arsenious acid include those capable of binding to an analyte will depend upon the analyte of interest, and for analytes having vicinal hydroxyl groups can include aryl or more preferably, a phenyl group.

In some embodiments, increasing analyte concentrations can result in increases in the amount of light of particular wavelengths that can be detected by a receiver associated with a sensor. In some embodiments, increasing analyte concentrations can result in decreases in the amount of light of particular wavelengths that can be detected by a receiver associated with a sensor. In some embodiments, increases in the concentration of analyte can result in increases in the amount of light of one wavelength that can be detected by a receiver associated with a sensor and decreases in the amount of light of another wavelength that can be detected by a receiver associated with a sensor.

In some embodiments, the methods described herein can be applied to fluorescence-based analyte sensors which produce a fluorescent response in relation to a change in analyte concentration that the sensor is exposed to. Suitable analyte sensors include analyte sensors having a polymeric external surface on at least a portion of the sensor. Polymeric materials that can be utilized as a portion of the external surface include hydrophobic polymers such as polyolefin (for example polyethylene and polypropylene), polycarbonate, polysulfone, and fluorocarbons. Sensors can be constructed in various ways, appropriate to the sensing chemistry/technique that is utilized by the sensor. In one embodiment of an optical sensor, such as a sensor producing a fluorescent response in relation to the analyte concentration to which the sensor is exposed, the optical sensor can have a porous polymeric outer surface for a portion of the sensor assembly. Such sensors are described in, for example, U.S. patent application Ser. No. 12/026,396, to Markle, et al., incorporated herein by reference in its entirety.

In some embodiments, a sensor can include an insoluble polymeric matrix immobilizing the analyte sensitive material or other components of the sensor, which is sufficiently permeable to analytes of interest. Suitable polymeric matrix materials include those related to acrylic polymers. In some embodiments, fluorophores and/or binders/quenchers can be incorporated into the polymeric matrix.

Analyte Sensors—Construction

FIG. 1 shows an exemplary sensor 2 comprising an optical fiber 10 with a distal end 12 disposed in a porous membrane sheath 14. The optical fiber 10 has cavities, such as holes 6A, in the fiber optic wall that can be formed by, for example, mechanical means such as drilling or cutting. The holes 6A in the optical fiber 10 can be filled with a suitable compound, such as a polymer. In some embodiments, the polymer is a hydrogel 8. In other embodiments of the sensor 2 as shown in FIG. 2, the optical fiber 10 does not have holes 6A, and instead, the hydrogel 8 is disposed in a space distal to the distal end 12 of the optical fiber 10 and proximal to the mirror 23. In some embodiments, the sensor 2 is a glucose sensor. In some embodiments, the glucose sensor is an intravascular glucose sensor.

In some embodiments, the porous membrane sheath 14 can be made from a polymeric material such as polyethylene, polycarbonate, polysulfone or polypropylene. Other materials can also be used to make the porous membrane sheath 14 such as zeolites, ceramics, metals, or combinations of these materials. In some embodiments, the porous membrane sheath 14 may be nanoporous. In other embodiments, the porous membrane sheath 14 may be microporous. In still other embodiments, the porous membrane sheath 14 may be mesoporous.

In some embodiments as shown in FIG. 2, the porous membrane sheath 14 is attached to the optical fiber 10 by a connector 16. For example, the connector 16 can be an elastic collar that holds the porous membrane sheath 14 in place by exerting a compressive force on the optical fiber 10, as shown in FIG. 2. In other embodiments, the connector 16 is an adhesive or a thermal weld.

In some embodiments as shown in FIG. 1, a mirror 23 and thermistor 25 can be placed within the porous membrane sheath 14 distal the distal end 12 of the optical fiber 10. Thermistor leads 27 can be made to run in a space between the optical fiber 10 and porous membrane sheath 14. Although a thermistor 25 is shown, other devices such as a thermocouple, pressure transducer, an oxygen sensor, a carbon dioxide sensor or a pH sensor for example can be used instead.

In some embodiments as shown in FIG. 2, the distal end 18 of the porous membrane sheath 14 is open and can be sealed with, for example, an adhesive 20. In some embodiments, the adhesive 20 can comprise a polymerizable material that can fill the distal end 18 and then be polymerized into a plug. Alternatively, in other embodiments the distal end 18 can be thermally welded by melting a portion of the polymeric material on the distal end 18, closing the opening and allowing the melted polymeric material to resolidify. In other embodiments as shown in FIG. 1, a polymeric plug 21 can be inserted into the distal end 18 and thermally heated to weld the plug to the porous membrane sheath 14. Themoplastic polymeric materials such as polyethylene, polypropylene, polycarbonate and polysulfone are particularly suited for thermal welding. In other embodiments, the distal end 18 of the porous membrane sheath 14 can be sealed against the optical fiber 10.

After the porous membrane sheath 14 is attached to the optical fiber 10 and the distal end 18 of the porous membrane sheath 14 is sealed, the sensor 2 can be vacuum filled with a first solution comprising a monomer, a crosslinker and a first initiator. Vacuum filling of a polymerizable solution through a porous membrane and into a cavity in a sensor is described in detail in U.S. Pat. No. 5,618,587 to Markle et al.; incorporated herein in its entirety by reference thereto. The first solution is allowed to fill the cavity 6 within the optical fiber 10.

In some embodiments, the first solution is aqueous and the monomer, the crosslinker and the first initiator are soluble in water. For example, in some embodiments, the monomer is acrylamide, the crosslinker is bisacrylamide and the first initiator is ammonium persulfate. In other embodiments, the monomer is dimethylacrylamide or N-hydroxymethylacrylamide. By increasing the concentrations of the monomer and/or crosslinker, the porosity of the resulting gel can be decreased. Conversely, by decreasing the concentrations of the monomer and/or crosslinker, the porosity of the resulting gel can be increased. Other types of monomers and crosslinkers are also contemplated. In other embodiments, the first solution further comprises an analyte indicator system comprising a fluorophore and an analyte binding moiety that functions to quench the fluorescent emission of the fluorophore by an amount related to the concentration of the analyte. In some embodiments, the fluorophore and analyte binding moiety are immobilized during polymerization, such that the fluorophore and analyte binding moiety are operably coupled. In other embodiments, the fluorophore and analyte binding moiety are covalently linked. The indicator system chemistry may also be covalently linked to the polymeric matrix.

In some embodiments, after the sensor 2 is filled with the first solution, the optical fiber 10 and the first solution filled porous membrane sheath 14 and cavity 6 are transferred to and immersed into a second solution comprising a second initiator. In some embodiments, the second solution is aqueous and the second initiator is tetramethylethylenediamine (TEMED). In some embodiments, the second solution further comprises the same fluorescent dye and/or quencher found in the first solution and in substantially the same concentrations. By having the fluorescent dye and quencher in both the first solution and the second solution, diffusion of fluorescent dye and quencher out of the first solution and into the second solution can be reduced. In some embodiments where a second solution is used, the second solution further comprises monomer in substantially the same concentration as in the first solution. This reduces diffusion of monomer out of the first solution by reducing the monomer gradient between the first solution and the second solution.

In some embodiments, at or approximately at the interface between the first and second solutions, the first initiator and the second initiator can react together to generate a radical. In some embodiments, the first initiator and the second initiator react together in a redox reaction. In other embodiments, the radical can be generated by thermal decomposition, photolytic initiation or initiation by ionizing radiation. In these other embodiments, the radical may be generated anywhere in the first solution. Once the radical is generated, the radical can then initiate polymerization of the monomer and crosslinker in the first solution.

When the radical is generated via a redox reaction as described herein, the polymerization proceeds generally from the interface between the first and second solutions to the interior of the porous membrane sheath 14 and towards the cavity in the optical fiber 10. Rapid initiation of polymerization can help reduce the amount of first initiator that can diffuse from the first solution and into the second solution. Reducing the amount of first initiator that diffuses out of the first solution helps reduce polymerization of monomer outside the porous membrane sheath 14 which helps in forming a smooth external surface. Polymerization of the monomer and crosslinker results in a hydrogel 8 that in some embodiments substantially immobilizes the indicator system, forming the sensor 2. Further variations on polymerization methodologies are disclosed in U.S. Patent Publ. No. 2008/0187655; incorporated herein in its entirety by reference thereto.

With reference to FIG. 3A, in certain embodiments, the glucose sensor 2 is a solid optical fiber with a series holes 6A drilled straight through the sides of the optical fiber. In certain embodiments, the holes 6A are filled with the hydrogels 8. In certain embodiments, the series of holes 6A that are drilled through the glucose sensor 2 are evenly spaced horizontally and evenly rotated around the sides of the glucose sensor 2 to form a spiral or helical configuration. In certain embodiments, the series of holes 6A are drilled through the diameter of the glucose sensor 2. With reference to FIG. 3B, in certain embodiments, the glucose sensor 2 is a solid optical fiber with a series of holes 6A drilled through the sides of the fiber at an angle. In certain embodiments, the series of holes 6A drilled at an angle, which are filled with hydrogel 8, are evenly spaced horizontally and evenly rotated around the sides the glucose sensor 2. With reference to FIG. 3C, in certain embodiments, the optical fiber comprises a groove 6B along the length of the optical fiber, wherein the groove 6B is filled with hydrogel 8. In certain embodiments, the depth of the groove 6B extends to the center of the optical fiber. In certain embodiments, the groove 6B spirals around the optical fiber. In certain embodiments, the groove 6B spirals around the optical fiber to complete at least one rotation. In certain embodiments, the groove spirals 6B around the optical fiber to complete multiple rotations around the optical fiber.

With reference to FIG. 3D, in certain embodiments, the glucose sensor 2 is a solid optical fiber with triangular wedges 6C cut from the fiber. In certain embodiments, the triangular wedge areas 6C are filled with hydrogel 8. In certain embodiments, the triangular wedges cut-outs 6C are evenly spaced horizontally and around the sides of the glucose sensor 2. In certain embodiments, all light traveling in the glucose sensor 2 is transmitted through at least one hole 6A or groove 6B filled with hydrogel 8.

In certain embodiments, as illustrated in FIG. 4, the glucose sensor 2 comprises an optical fiber 10 having a distal end 12, an atraumatic tip portion 134 having a proximal end 136 and a distal end 138, a cavity 6 between the distal end 12 of the optical fiber 10 and the proximal end 136 of the atraumatic tip portion 134, and a rod 140 connecting the distal end 12 of the optical fiber 10 to the proximal end 136 of the atraumatic tip portion 134. A hydrogel 8 containing glucose sensing chemistry, for example a fluorophore and quencher, fills the cavity 6. Covering the hydrogel filled cavity 6 is a selectively permeable membrane 14 that allows passage of glucose into and out of the hydrogel 8. Although these embodiments are described using a glucose sensor 2, it should be understood by a person of ordinary skill in the art that the sensor 2 can be modified to measure other analytes by changing, for example, the sensing chemistry, and if necessary, the selectively permeable membrane 14. The proximal portion of the sensor 2 comprises the proximal portion of the optical fiber 10. In some embodiments, the diameter, D1, of the distal portion of the sensor 2 is greater than the diameter, D2, of the proximal portion of the sensor 2. For example, the diameter D1 of the distal portion of the sensor 2 can be between about 0.0080 inches and 0.020 inches, while the diameter D2 of the proximal portion of the sensor 2 can be between about 0.005 inches to 0.015 inches. In some embodiments, the diameter D1 of the distal portion of the sensor 2 is about 0.012 inches, while the diameter D2 of the proximal portion of the sensor 2 is about 0.010 inches.

In some embodiments, the glucose sensor 2 includes a temperature sensor 25, such as thermocouple or thermistor. The temperature sensor 25 can measure the temperature of the hydrogel 8 and glucose sensing chemistry system. The temperature sensor 25 is particularly important when the glucose sensing chemistry, such as a fluorophore system, is affected by temperature change. For example, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of glucose concentration, as more fully described below.

In certain embodiments, the hydrogels are associated with a plurality of fluorophore systems. In certain embodiments, the fluorophore systems comprise a quencher with a glucose receptor site. In certain embodiments, when there is no glucose present to bind with the glucose receptor, the quencher prevents the fluorophore system from emitting light when the dye is excited by an excitation light. In certain embodiments, when there is glucose present to bind with the glucose receptor, the quencher allows the fluorophore system to emit light when the dye is excited by an excitation light.

In certain embodiments, the emission produced by the fluorophore system varies with the pH of the solution (for example, blood), such that different excitation wavelengths (one exciting the acid form of the fluorophore and the other the base form of the fluorophore) produce different emissions signals. In preferred embodiments, the ratio of the emission signal from the acid form of the fluorophore over the emission signal from the base form of the fluorophore is related to the pH level of the blood; the simultaneous measurement of glucose and pH is described in detail in U.S. Patent Publication No. 2008/0188722 (incorporated herein in its entirety by reference thereto). In certain embodiments, an interference filter is employed to ensure that the two excitation lights are exciting only one form (the acid form or the base form) of the fluorophore.

Figure 5:
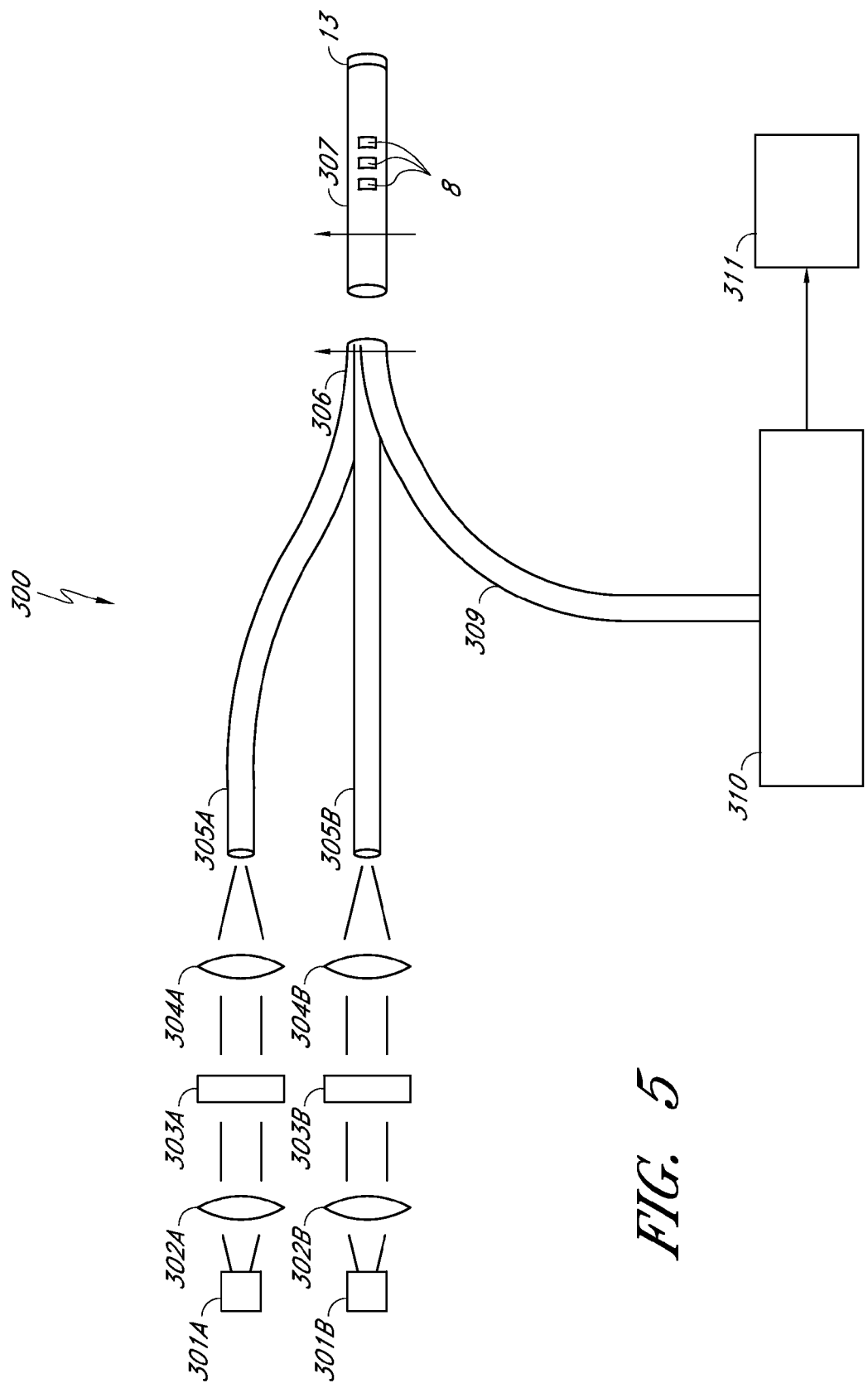
FIG. 5 schematically illustrates an analyte measurement system comprising two excitation light sources and a microspectrometer and/or spectrometer.

Variations optical sensing systems, light sources, hardware, filters, and detection systems are described in detail in U.S. Publication No. 2008/0188725; incorporated herein in its entirety by reference thereto. See e.g., FIG. 5, wherein certain embodiments comprise at least two light sources. In certain embodiments, the light sources 301A, 301B generate excitation light that is transmitted through a collimator lens 302A, 302B. In certain embodiments, the resulting light from collimator lens 302A, 302B is transmitted to interference filters 303A, 303B. In certain embodiments, the resulting light from interference filters 303A, 303B is focused by focusing lens 304A, 304B into fiber optic lines 305A, 305B.

In certain embodiments, fiber optic lines may be a single fiber or a bundle of fibers. In certain embodiments, the fiber optic line 309 may be a single fiber or a bundle of fibers. In certain embodiments, fiber optic lines 305A, 305B, 309 are bundled together at junction 306 and are connected at glucose sensor 307. The glucose sensor 307 comprises hydrogels 8.

In certain embodiments, the emission light and the excitation light are reflected off the mirror 13 and into the fiber optic line 309. In certain embodiments, the fiber optic line 309 is connected to microspectrometer 310 that measures the entire spectrum of light in the glucose measurement system 300. The microspectrometer 310 may be coupled to a data processing module 311, e.g., the sensor control unit and/or receiver/display unit. In certain embodiments, the ratio of emission light over the corresponding excitation light is related to the concentration of glucose. In certain embodiments, the ratio of the emissions light (for example, the acid form) produced by the first excitation light over the emission light (for example, the base form) produced by the second excitation light is related to pH levels in the test solution, for example blood.

In certain preferred embodiments, the microspectrometer is the UV/VIS Microspectrometer Module manufactured by Boehringer Ingelheim. Any microspectrometer can be used. Alternatively, the microspectrometer could be substituted with other spectrometer, such as those manufactured by Ocean Optic Inc.

Figure 6:
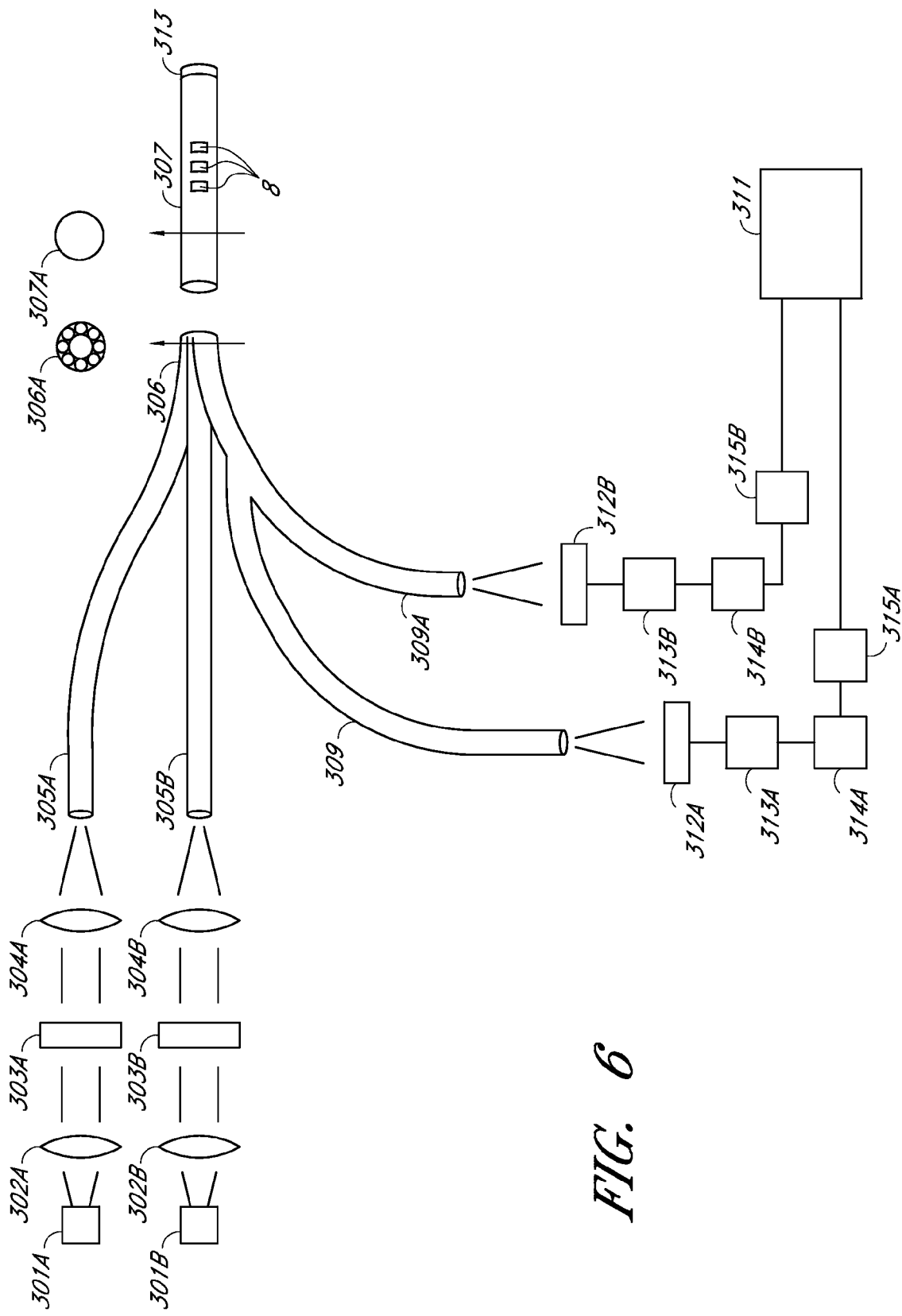
FIG. 6 schematically illustrates an analyte measurement system comprising two excitation light sources and two detectors.
Figure 7:
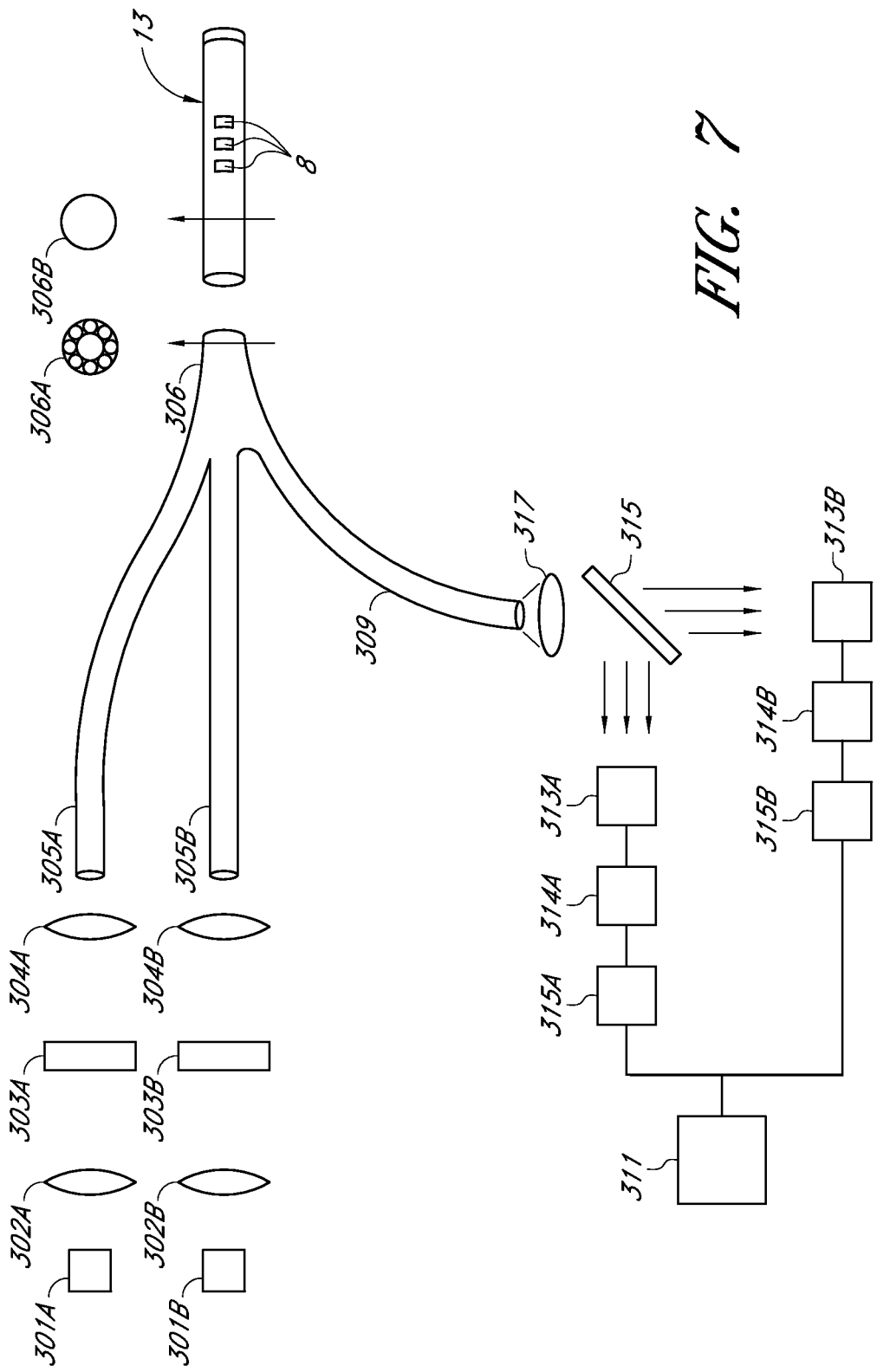
FIG. 7 schematically illustrates an analyte measurement system comprising two excitation light sources, a beam splitter, and two detectors.

The systems described above with reference to FIG. 5 can be augmented by comprising a light sensitive module comprising two interference filters 312A, 312B and two detectors 313A, 313B as shown in FIG. 6. In certain embodiments, substantially half of the emission light and half of the excitation light are transmitted from the glucose sensor into the fiber optic line 309 and the remainder of the emission light and the excitation lights are transmitted from the glucose sensor into the fiber optic line 309A. The interference filter 312A can be configured to block the excitation lights and allow the emission light to pass to detector 313A where the emission light is measured. The signal produced by the detector 313A can be amplified by the amplifier 314A and converted into a digital signal by analog-to-digital converter 315A and transmitted to a data processing module 311. The interference filter 312B can be configured to block the emission light and allow the excitation lights to pass to detector 313B where the excitation light is measured. In certain embodiments, the signal produced by the detector 313B can be amplified by the amplifier 314B and converted into a digital signal by analog-to-digital converter 315B and transmitted to a data processing module 311. In some embodiments, ratiometric calculations may be employed to substantially eliminate or reduce non-glucose related factors affecting the intensity of the measured emission light and measured excitation light. In certain embodiments, the measured emission light is divided by the measured excitation light, wherein such calculations substantially eliminate or reduce non-analyte (e.g. non-glucose) related factors affecting the intensity of the lights. Alternatively, the bifurcated fibers 309, 309A can be substituted with a single fiber or fiber bundle 309 and a beam splitter 315, as illustrated for example in FIG. 7.

In some embodiments, different sensor technologies, different analyte-responsive materials, and/or different sensor constructs can be used with the methods disclosed herein. Suitable analyte-responsive indicators that can be utilized in a sensor used with preferred embodiments of the present invention include those which exhibit a change in the light emitted, transmitted, reflected, or absorbed in a reproducible and reversible fashion in response to changes in the concentration of analyte exposed to the sensor. Changes in the light can include an increase in detectable light, a decrease in detectable light or a change in the spectrum of the detectable light. In some embodiments, changes in the concentration of analyte the sensor is exposed to can result in changes in the amount of analyte bound (e.g. adsorbed, absorbed, chemisorbed, etc.) to the chemical species present in the analyte sensor. In some embodiments the sensing technology/mechanism is based on a fluorophore operably coupled to a quencher binding moiety, as described in detail below. In certain such embodiments, the quencher may reversibly bind the analyte of interest and such reversible binding effects the fluorescent response of the fluorophore. In other embodiments, the sensing mechanism may be based on lifetime chemistry as described in detail below.

Fluorophore/Quencher Based Analyte Sensing Mechanisms

In some embodiments, a sensor can utilize a chemical species having a measurable sensitivity to compounds having multiple hydroxyl groups, such as glucose or other saccharides and saccharides derivatives. In preferred embodiments a sensor can utilize sensor elements comprising SNARF-1, SNAFL-1, TSPP, and HPTS and derivatives thereof, as well as HPTS-CysMA, HPTS-LysMA, and polymers comprised thereof as fluorescent compounds, as described in U.S. patent application Ser. Nos. 11/671,880 and 12/027,158, both to Markle, et al., and U.S. Pat. No. 7,417,164, to Suri. Preferred embodiments can also utilize binders/quenchers having viologen groups, pyridinium groups, boronic acid groups, viologen-boronic acid adducts, pyridinium-boronic acid adducts, and other derivatives of boronic acid, arsenious acid, or germanic acid, including benzylboronic acid and derivatives of benzylboronic acid. Particular compounds suitable as binders/quenchers include 3,3'-oBBV and compounds having the following structures, as disclosed in U.S. patent application Ser. Nos. 12/113,876 and 12/172,059, both to Gamsey, et al., and U.S. Pat. No. 7,417,164, to Suri, incorporated by reference herein in their entireties:

Compound T-1

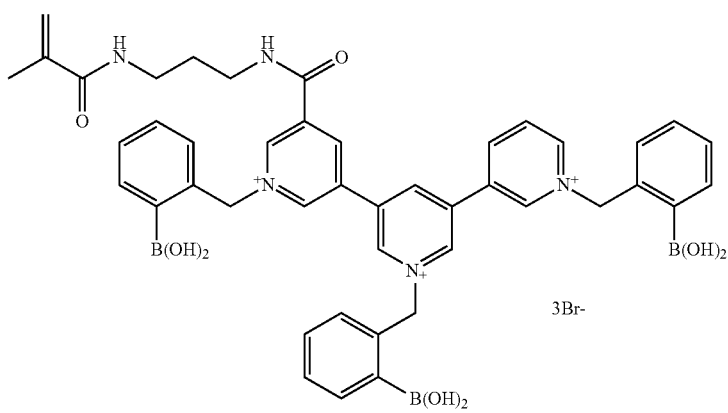

-continued
Compound T-2
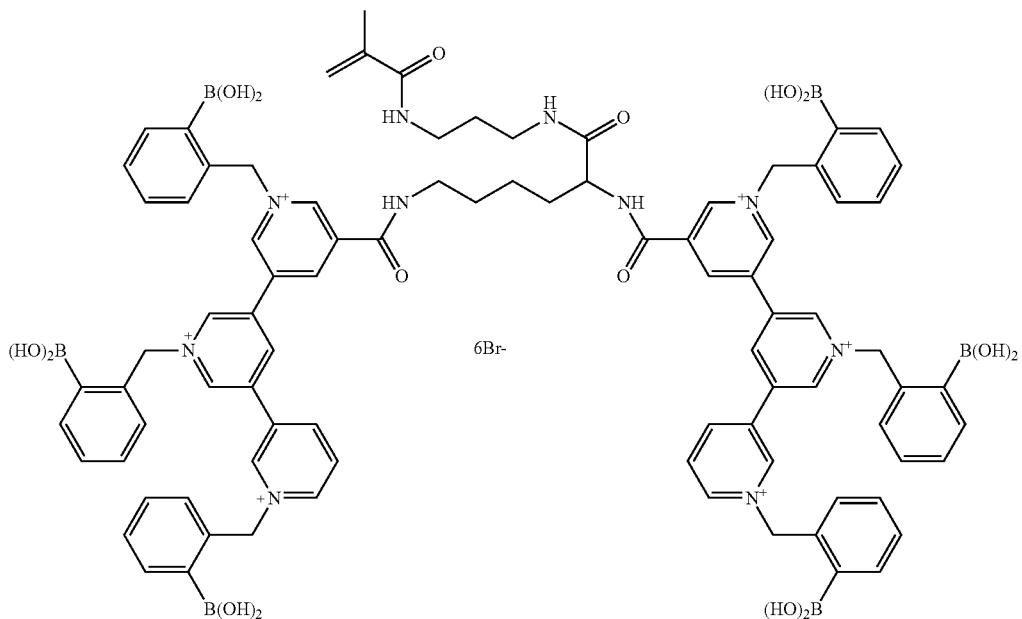
Compound T-1
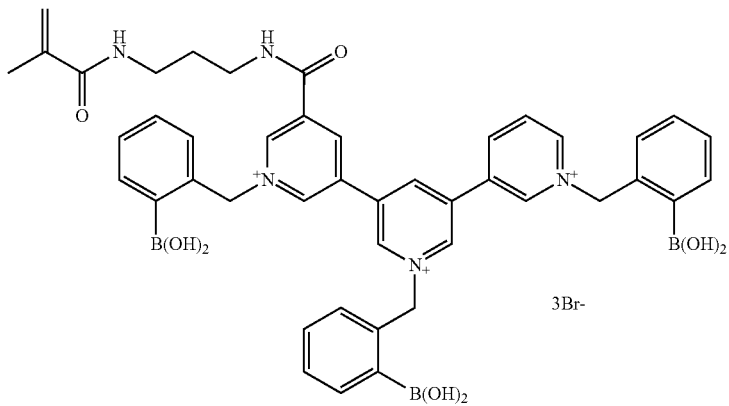
Compound T-2
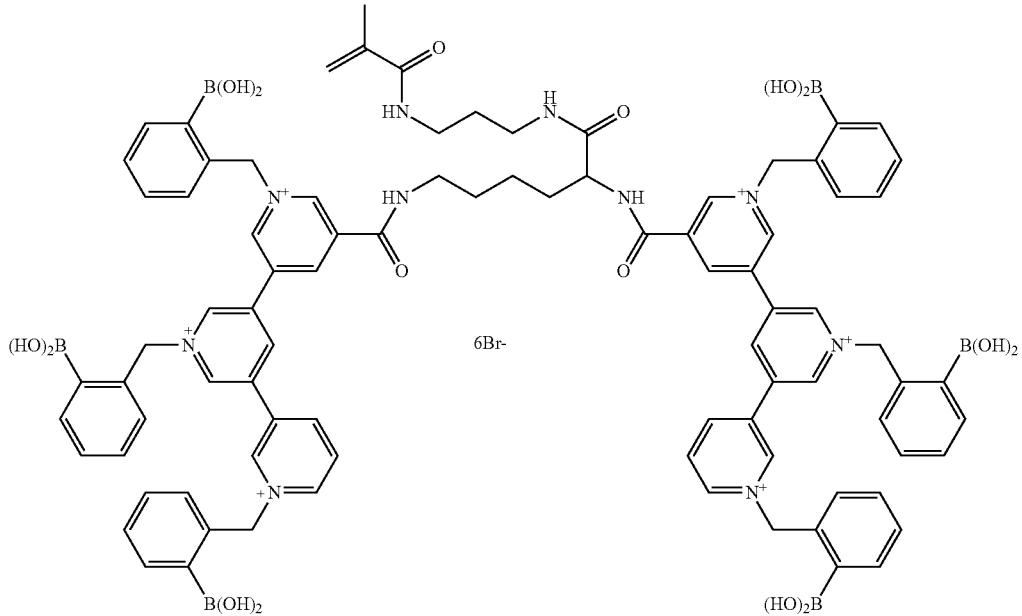

-continued
Compound P-1
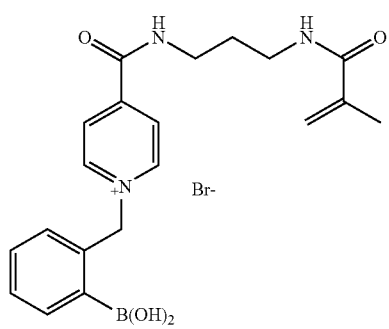
Compound P-2
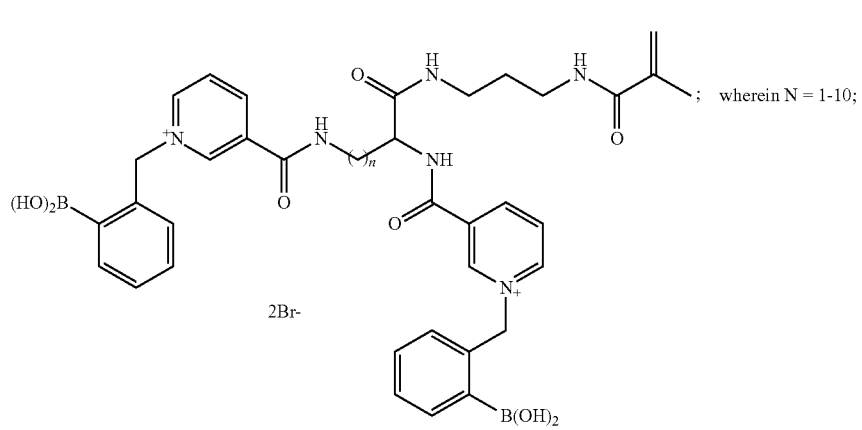
; wherein N = 1-10;
Compound B
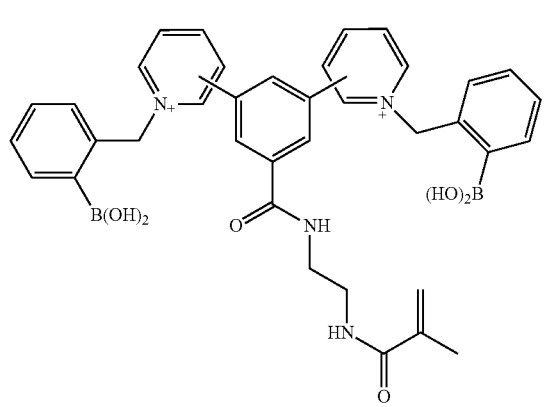
Compound C
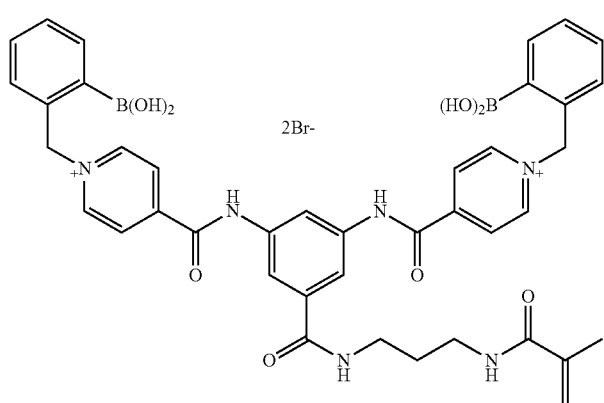

Compounds B-1, B-2, B-3, B-4
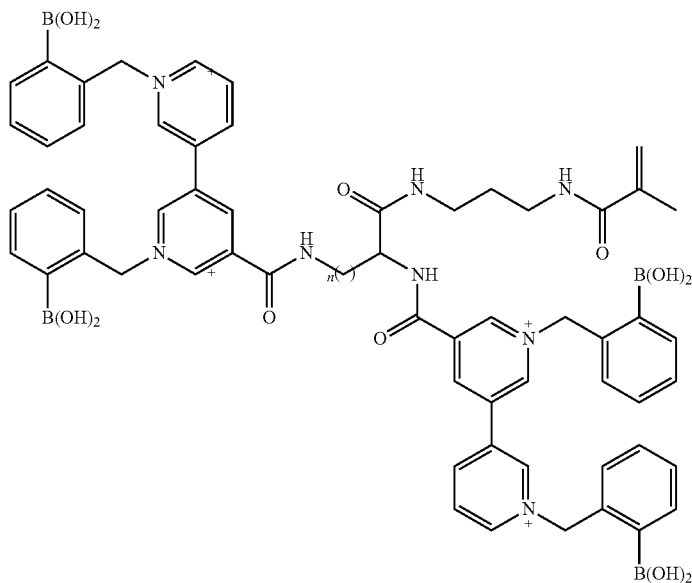
B-1 (n = 1)
B-2 (n = 2)
B-3 (n = 3)
B-4 (n = 4)
Compound B-C
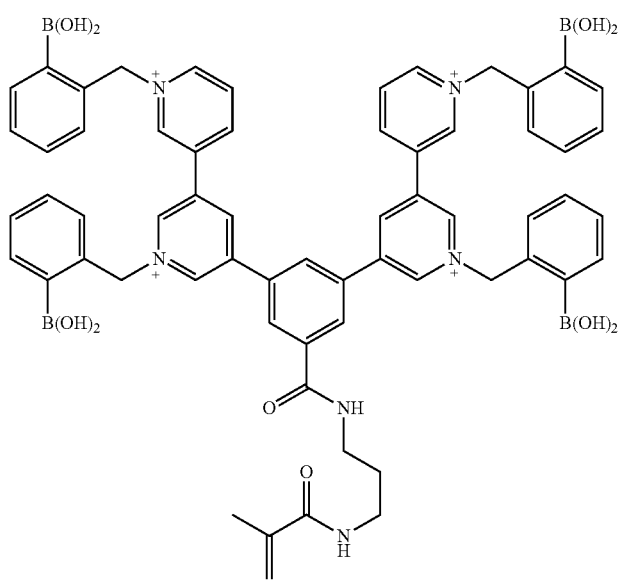
B-C Compound Q-4

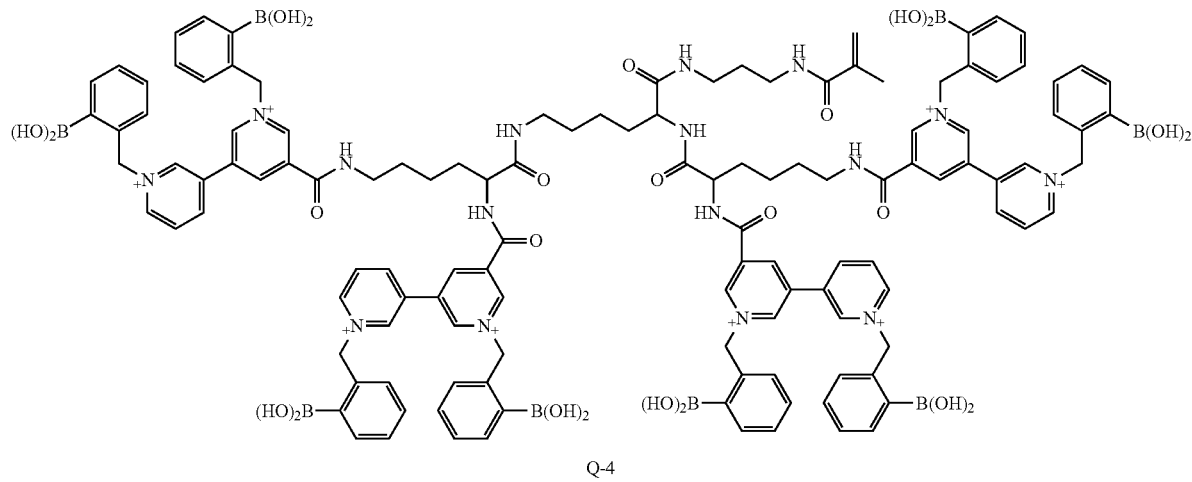

Q-4

In some embodiments, a sensor can utilize a chemical species having a measurable sensitivity to analytes other than those having vicinal hydroxyl groups, such as potassium, sodium, lithium, hydrogen ion (pH), oxygen and $CO_2$. Suitable analyte sensitive materials include fluorescent compounds and quenchers/binders such as N-(9, anthryl-methyl) monoaza-18-Crown-6; cuomaro crypand of 4,7,13,16,21,24-Hexaoxa-1,10-diazabicyclo[8.8.8]hexacosane); comaro crypand of 4,7,13,16,21-Pentaoxa-1,10-diazabicyclo[8.8.5]tricosane; cuomaro crypand of 4,7,13,18-Tetraoxa-1,10-diazabicyclo[8.5.5]eicosane in the presence of 4,7,13,16,21-Pentaoxa-1,10-diazabicyclo[8.8.5]tricosane; hydroxipyrene trisulfonic acid; platinum tetra (penta phenyl porphyrinel); 9,10 diphenyl anthracene; pyrenebutyric acid; and trist(4,7 diphenyl 1, 10 phenanthroline) ruthenium (II) perchlorate, as described in U.S. Pat. No. 5,176,882 to Gray, et al., incorporated herein by reference in its entirety, as well as diazotized m-aminophenylboronic acid (APB) and naphthol derivatives; fluorescent dyes derived from APB and dansyl chloride, as described in U.S. Pat. No. 5,137,833, to Russell, incorporated herein by reference in its entirety, and other dyes, binding moieties, and quenchers as understood by those having skill in the art.

Lifetime Chemistry

In another embodiment, glucose concentrations can be determined by exploiting the phenomena of fluorescence resonance energy transfer (FRET). FRET is the transfer of energy from a donor fluorophore to an acceptor molecule. FRET occurs when the donor fluorophore, which fluoresces at a wavelength absorbed at least in part by the acceptor molecule, is in close proximity to the acceptor such that the donor fluorophore can transfer energy to the acceptor through molecular interactions. The fluorescence lifetime of the fluorophore, where the fluorescence lifetime is the time the fluorophore remains in the excited state, is altered by FRET. Thus, measuring the fluorescence lifetime of the fluorophore allows one to determine whether the fluorophore is bound to the acceptor.

Lifetime can be measured by using a time-domain method where the fluorophore is excited by a brief pulse of excitation light and the fluorescence intensity is measured over time. The excitation pulse can be a pulse from a laser with a duration in the picoseconds range up to a duration of about a few nanoseconds. In other embodiments, the pulse duration can be greater than about a few nanoseconds. The fluorescence intensity of the fluorophore as a function of time is given by the equation:

$$I(t) = I_0 * \exp(-t/\tau) \quad \text{Equation 1}$$

Figure 8:
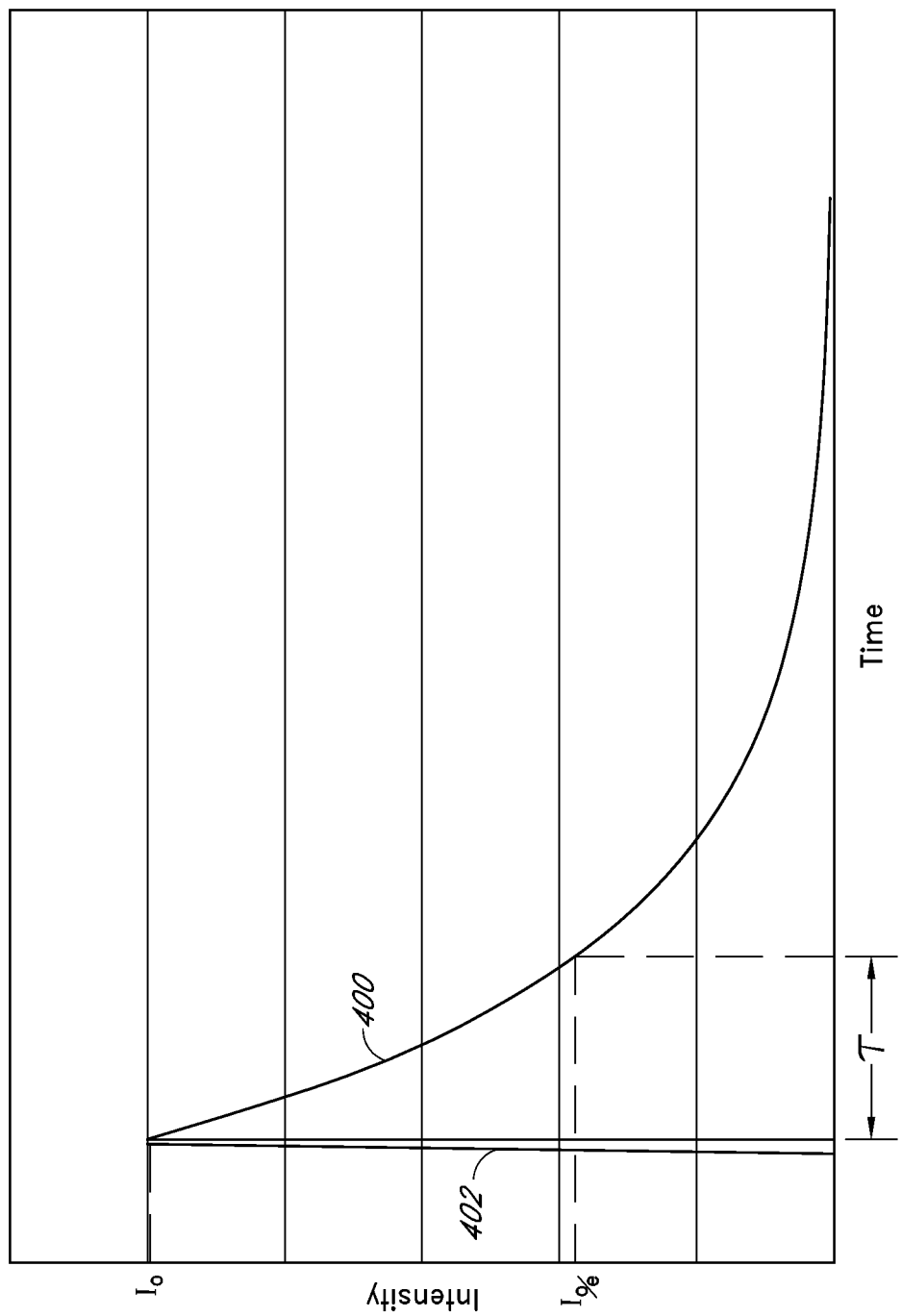
FIG. 8 displays a graph of the decay of the fluorescent emission over time after a pulse of excitation light.

I(t) is the fluorescence intensity at time (t), $I_0$ is the initial intensity after excitation and $\tau$ is the fluorescence lifetime which is defined as the time required for I(t) to decay to $I_0/e$. Equation 1 is applicable to a fluorophore with a single exponential decay of fluorescence and a lifetime that is substantially longer than the excitation pulse. FIG. 8 shows a graph of the decay of the fluorescent emission 400 over time after a pulse of excitation light 402. The time it takes the initial intensity, $I_0$, to drop to $I_0/e$ is equal to the lifetime, $\tau$.

An alternative method of measuring lifetime is by a frequency-domain method where the fluorophore is excited by a frequency modulated excitation light. The fluorescence lifetime, $\tau$, can be determined by measuring the phase shift of the emission from the fluorophore relative to the excitation light, or by measuring the modulation ratio, using the following equations:

$$\tau_\phi = \omega^{-1} * \tan(\phi) \quad \text{Equation 2}$$

$$\omega = 2\pi f \quad \text{Equation 3}$$

$$\tau_M = \omega^{-1} * (M^{-2} - 1)^{1/2} \quad \text{Equation 4}$$

$$M = \frac{(AC/DC)_{EM}}{(AC/DC)_{EX}} \quad \text{Equation 5}$$

Figure 9:
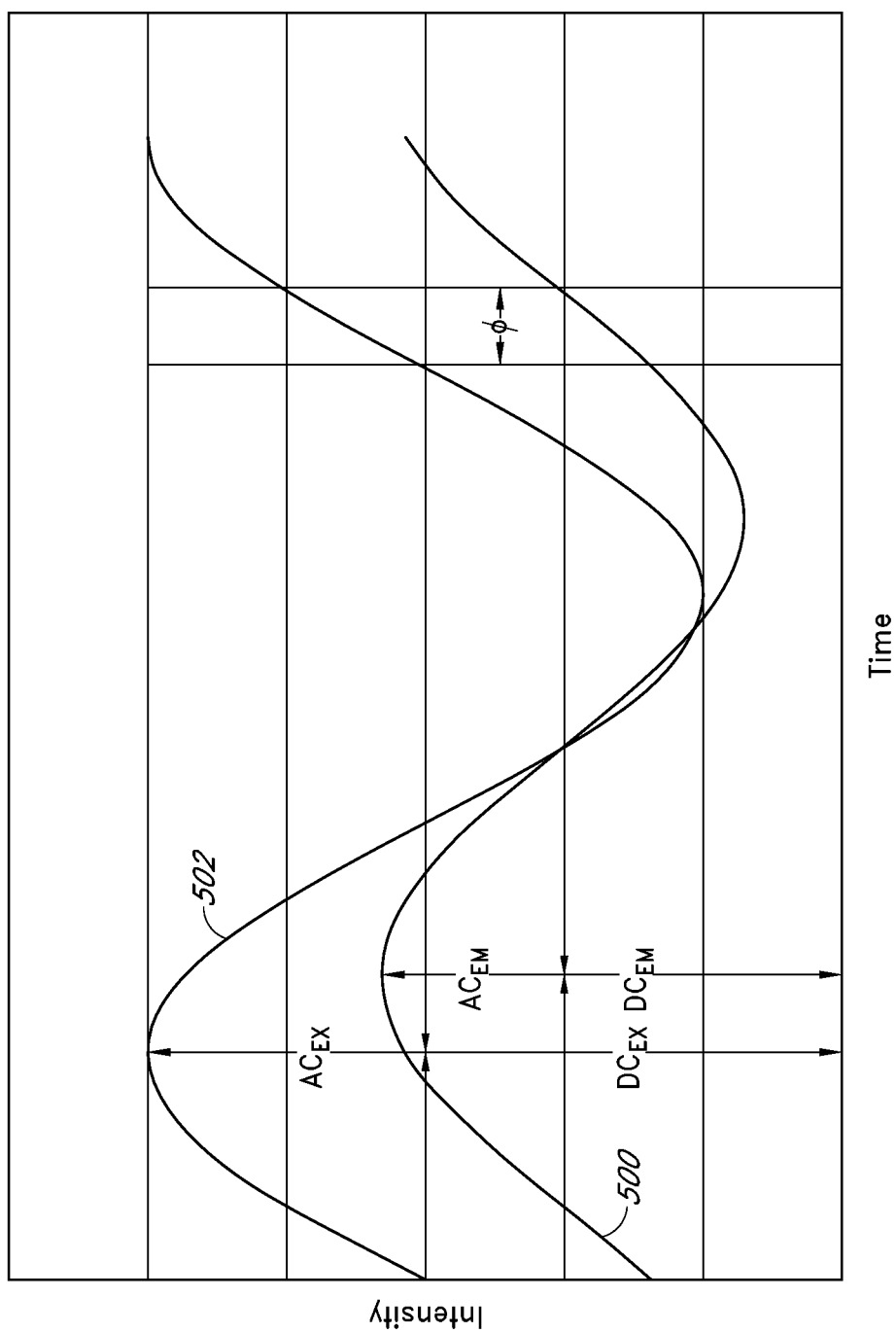
FIG. 9 displays a graph showing the relationship between the emission signal and the excitation signal.

$\tau_\phi$ is the lifetime determined by measuring the phase shift, $\phi$. $\omega$ is the angular frequency of the frequency modulated excitation light and f is the linear frequency. $\tau_M$ is the lifetime determined by measuring the modulation ratio, M. AC is the magnitude of the alternating portion of the signal, or the amplitude of the wave, while DC is the amplitude of the DC portion of the signal. EM refers to the emission signal, and EX refers to the excitation signal. FIG. 9 is a graph showing the relationship between the emission signal 500 and the excitation signal 502 and the variables described in Equations 2-5.

Preferred binding assay configurations for use in the sensor include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance.

In some preferred embodiments of the sensor of the invention incorporates a competitive, reagent limited binding assay which generates an optical readout using the technique of fluorescence resonance energy transfer. In this assay format the analyte analog is labeled with a first chromophore and the analyte binding agent is labeled with a second chromophore. One of the first and second chromophores acts as a donor chromophore and the other acts as an acceptor chromophore. It is an important feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as FRET, with the result that a proportion of the fluorescent signal emitted by the donor chromophore is quenched and, in some instances, that the acceptor chromophore emits fluorescence. Fluorescence resonance energy transfer will generally only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labeled analyte analog is displaced from binding to the analyte binding agent. The intensity or lifetime of the fluorescent signal emitted from the donor chromophore thus correlates with the concentration of analyte in the fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to replace the sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp 21-30) describe a homogeneous assay method for the measurement of glucose based on fluorescence resonance energy transfer between a labeled glucose analog (FITC labeled dextran) and a labeled glucose binding agent (rhodamine labeled concanavalin A). In all of these configurations the acceptor and donor chromophores/quenchers can be linked to either the binding agent or the analyte analog.

Fluorescence lifetime or fluorescence intensity measurements may be made. As described in Lakowitz et al, Analytica Chimica Acta, 271, (1993), 155-164, fluorescence lifetime may be measured by phase modulation techniques.

Figure 10:
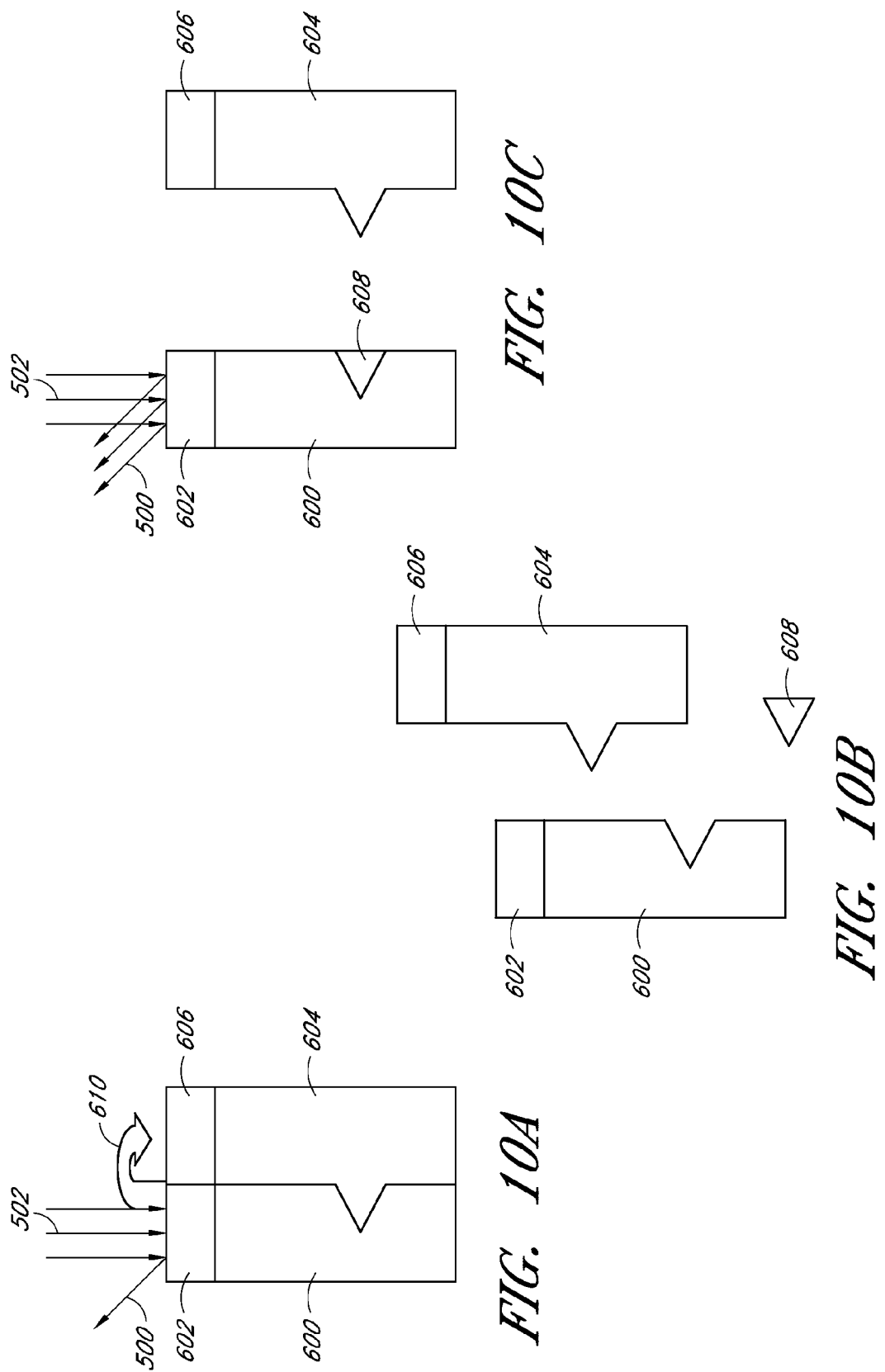
FIGS. 10A, 10B, and 10C schematically illustrate a competitive binding system for measuring glucose using FRET which comprises a glucose binding molecule linked to a donor fluorophore and a glucose analog linked to an acceptor molecule.
Figure 15:
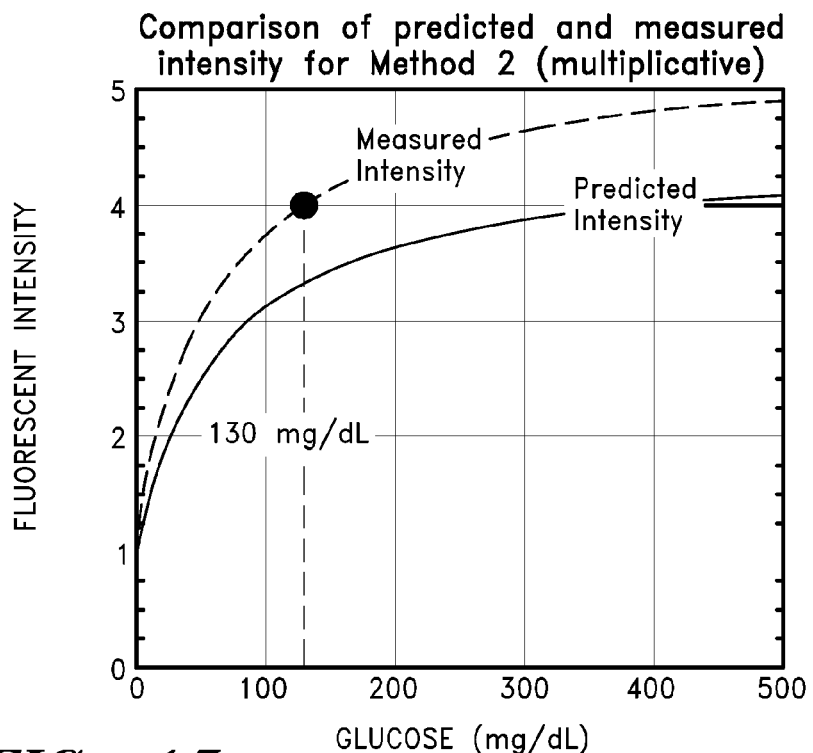
FIG. 15 displays a comparison of predicted and measured intensity used in one-point in vivo adjustment of the Michaelis-Menten parameters according to Method 2 disclosed herein with a multiplicative correction factor CF.

In some preferred embodiments as shown in FIGS. 10A, 10B and 10C, a competitive binding system to measure glucose using FRET comprises a glucose binding molecule 600 linked to a donor fluorophore 602 and a glucose analog 604 linked to an acceptor molecule 606. The glucose binding molecule 600 is capable of binding with both glucose 608 and the glucose analog 604. As shown in FIG. 15A, when the glucose analog 604 is bound to the glucose binding molecule 600, the fluorescent emission 500 from the fluorophore 602 is reduced in magnitude and shifted in phase and lifetime by FRET 610 because the fluorophore 502 is in close proximity to the acceptor 606. In other embodiments, the fluorophore 602 is linked to the glucose analog 604 and the acceptor 606 is linked to the glucose binding molecule 600.

As shown in FIG. 15B, glucose 608 competes with the glucose analog 604 for the binding site on the glucose binding molecule 600. As shown in FIG. 15C, the glucose molecule 608 can displace the glucose analog 604 from the glucose binding molecule 600 so that the acceptor 606 does not alter the emission lifetime 500 of the fluorophore 602 via FRET 610.

In a system where there are a certain concentration of glucose binding molecules, glucose analogs and glucose molecules, an equilibrium will exist between the number of bound glucose molecules to the number of bound glucose analogs. A change in the number of glucose molecules in the system, changes the equilibrium between bound glucose molecules to bound glucose analogs. This in turn changes the mean lifetime of the fluorophore emission.

In some preferred embodiments, the system is excited by a frequency modulated excitation light less than approximately 1 MHz, between approximately 1 to 200 MHZ, or greater than approximately 200 MHz. In some embodiments, the frequency is approximately 0.05, 0.1, 1, 10, 20, 30, 40, 50, 60, 70, 80, 90, 100, 110, 120, 130, 140, 150, 160, 170, 180, 190 or 200 MHz. By measuring the degree of the phase shift of the system, an average FRET induced phase shift for the system can be determined which corresponds to an average lifetime value for the system as defined by Equations 2 and 3 described above. Both the phase shift and the lifetime values can be correlated to the glucose concentration. The magnitude of the phase shift is independent of the amplitude of the emission.

In other preferred embodiments, the system is excited by a pulse and the decay of the fluorescence is measured over time. The lifetime can be determined using Equation 1 described above, and glucose concentration can be correlated to the lifetime value.

In preferred embodiments, the glucose binding molecule with a donor fluorophore and the glucose analog with an acceptor can be substantially immobilized in the hydrogel described above such that diffusion of the glucose binding molecule and the glucose analog out of the hydrogel is substantially reduced. In addition, the sensor is configured to provide excitation light at a wavelength absorbed by the donor fluorophore as described above. In some embodiments, the excitation light is provided as a short pulse from a laser or a light emitting diode (LED). In other embodiments, the excitation light is frequency modulated. In some embodiments, the frequency modulated excitation light is provided by a laser. In some embodiments the frequency modulated excitation light is provided by a LED. The sensor also has a detector that detects the amplitude of the emission over time and/or the phase shift of the emission and/or the amplitudes of the AC and DC portions of the emission and excitation light. The detector can be a photodetector or multiple photodetectors. The excitation and emission light can be transmitted throughout the sensor via optical fibers.

Analyte Sensors—Immobilizing Matrix

Suitable sensors can also include an insoluble polymeric matrix immobilizing the analyte sensitive material or other components of the sensor, which is sufficiently permeable to the analyte of interest to allow accurate or reproducible readings. In preferred embodiments, the polymer matrix can be comprised of organic, inorganic or combinations of polymers thereof. The matrix may be composed of biocompatible materials. Alternatively, the matrix can be coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N', N"-tris(methacrylamidopropylsulfonamide), the quencher moiety is derived from an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and through complex formation with the fluorophore. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

Sensor Calibration

Although the analyte sensors disclosed herein, and in particular the glucose sensors, are not limited to enzymatic sensors, it has been discovered that the fluorescent response of these sensors to glucose concentration may be characterized by a modified version of the Michaelis-Menten equation from enzyme kinetics. This surprising finding may possibly be explained by analogizing the mechanism of action of these sensors to the basic principles of enzyme kinetics.

In basic enzyme kinetics, there is a substrate S which binds to a site on an enzyme E to form a complex ES. The enzyme undergoes a structural change in the course of the chemical reaction. Finally, there is a reaction product P which is formed by the binding of the substrate to the enzyme. This type of reaction sequence is described in Scheme I (Conners, K. A. *Binding Constants: The Measurement of Molecular Complex Stability*, John Wiley & Sons, Inc., New York, 1987).

Scheme I

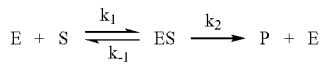

Figure 11:
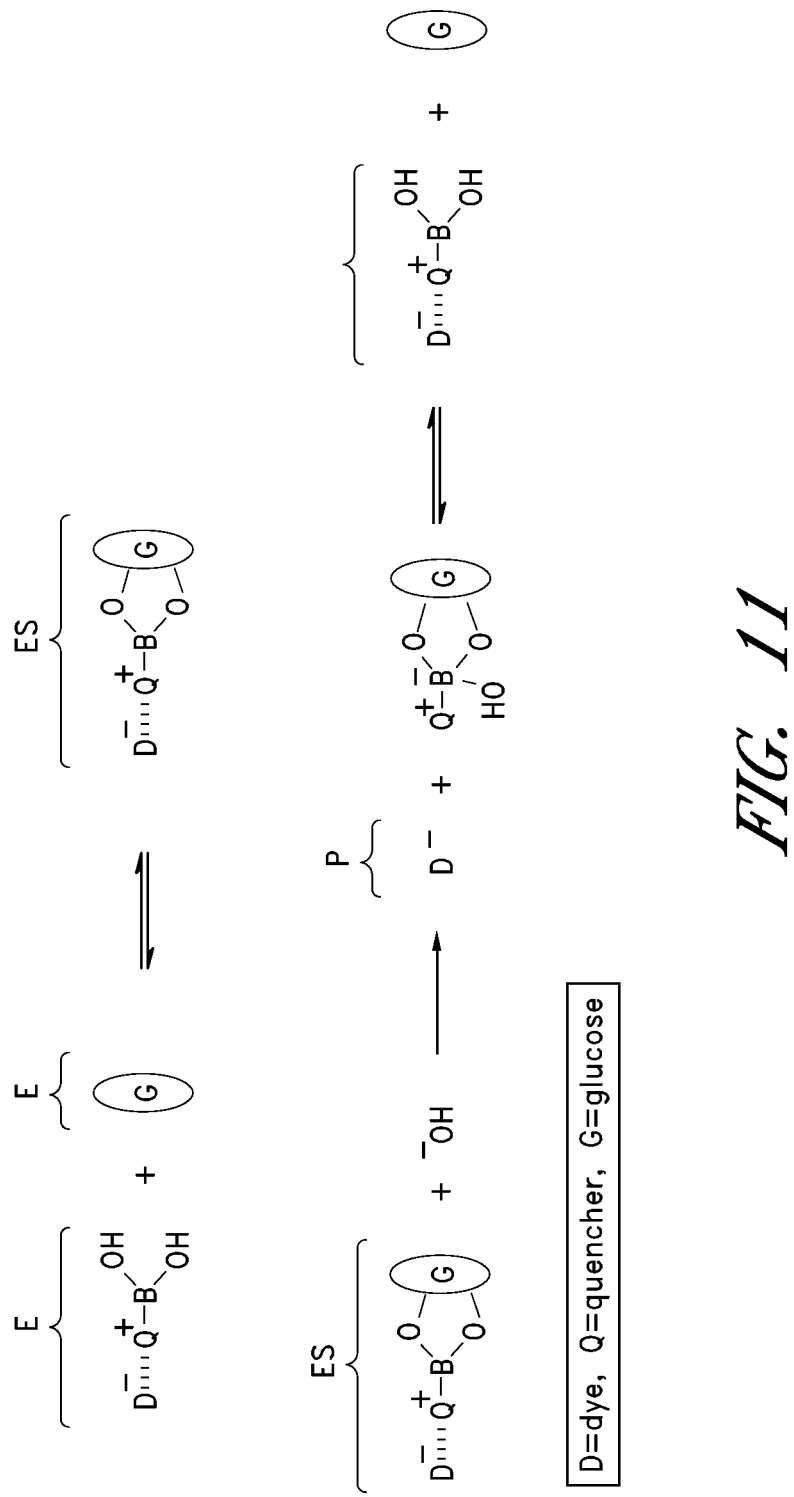
FIG. 11 displays an assignment of GluCath sensing components to those in Scheme I disclosed herein.

Accordingly, although the sensing technology described herein is not enzyme-based, one theory is that the molecular sensing components involved in the disclosed glucose sensing mechanisms may conform to a similar type of reaction scheme. In particular, FIG. 11 illustrates the mode of glucose binding in the GluCath sensor. The GluCath sensor referred to repeatedly herein refers to one preferred embodiment of a glucose sensor which comprises an HPTS-tri-CysMA dye operably coupled to a 3,3'-oBBV quencher, immobilized within a hydrogel disposed along the distal region of the optical fiber sensor. Reference to the GluCath sensor or system, however, should not be viewed as limiting in any way the scope of the disclosure or claims, but rather to illustrate a particular embodiment. All of the embodiments of glucose sensors or systems disclosed are intended to be covered by the claims appended hereto and not by a particular reference to a particular embodiment, such as by reference to the GluCath.

FIG. 11 illustrates how glucose binding in the GluCath sensor is theoretically analogous to Scheme I. Referring to FIG. 11, the species acting as the "enzyme" E is the dye/quencher-receptor complex, glucose is the substrate S, and the product P of the reaction is the liberated fluorescent dye D. In the GluCath system, an increase in the amount of the liberated fluorescent dye is associated with an increase in fluorescent intensity which is related to the glucose concentration.

Systems which follow the reaction mechanism described by Scheme I conform to what is commonly referred to as Michaelis-Menten kinetics and may be described by what is commonly referred to as the Michaelis-Menten equation. A derivation of the Michaelis-Menten equation from Scheme I is presented in Conners K. A. *Binding Constants: The Measurement of Molecular Complex Stability*, John Wiley & Sons, Inc., New York, 1987.

Using the pseudo steady-state approximation (Eq. 6.16), the complex, [ES], can be described by equation (6.17):

$$d[ES]/dt = k_1[E][S] - k_{-1}[ES] - k_2[ES] = 0 \quad (6.16)$$

$$[ES] = k_1[E][S]/(k_{-1} + k_2) \quad (6.17)$$

Since enzyme studies and the like are carried out with the condition $S_t \gg E_t$, we set $[S] = S_t$. Equation (6.17) is combined with the mass balance on enzyme, $E_t = [E] + [ES]$, to give:

$$[ES] = E_t S_t/(K_m + S_t) \quad (6.18)$$

where $$K_m = (k_{-1} + k_2)/k_1 \quad (6.19)$$

Figure 12:
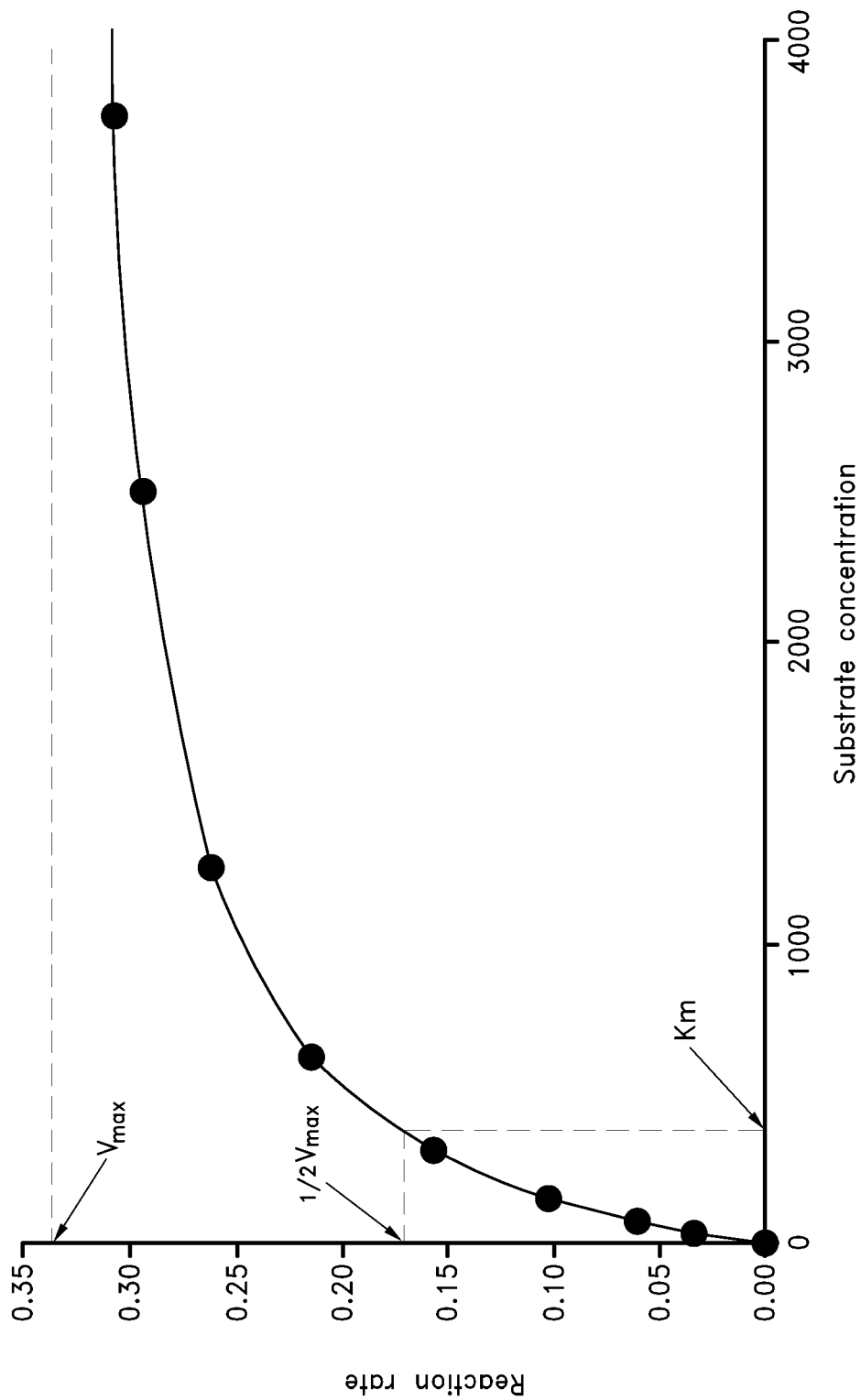
FIG. 12 displays a binding curve for an enzyme displaying Michaelis-Menten kinetics.

Combining Eq. (6.18) with the rate equation $v = k_2 \cdot [ES]$ gives the Michaelis-Menten equation (6.20):

$$v = V_{max} S_t/(K_m + S_t) \quad (6.20)$$

Where $V_{max} = k_2 E_t$ $K_m$ is known as the Michaelis-Menten constant. When $[S] = K_m$, then $v = V_{max}/2$, such that $K_m$ is defined as the substrate concentration at which the reaction velocity is half-maximal (FIG. 12). $K_m$ is unique for each enzyme-substrate pair and is thus a property of the particular system (e.g. the enzyme and the substrate). It may also exhibit a dependence on temperature and pH. The Michaelis constant is a measure of the affinity of the enzyme for its substrate.

Certain embodiments of the analyte sensors disclosed herein, and in particular the glucose sensors disclosed herein, require calibration before they can be properly used to generate meaningful readings of analyte concentration. A calibration equation is useful to establish the mathematical relationship between the measured fluorescent intensity and the analyte concentration being estimated. For example, for the case of a glucose sensor, once a calibration equation has been determined, it may be used to estimate a glucose concentration from a measured fluorescent intensity. Since it has been discovered that the fluorescent response of certain analyte sensors disclosed herein may be characterized by a modified version of the Michaelis-Menten equation, this equation may serve as the functional form for a calibration equation. In particular, for the case of GluCath sensor chemistry, the fluorescent response (I) of the chemistry to glucose (G), as shown graphically in FIG. 13 below, can be described by a modified form of the Michaelis-Menten equation in which three parameters (a, b, and c) are determined:

$$I = a + b \cdot G/(c + G)$$

where "a" is the fluorescent signal intensity in the absence of glucose, "b" determines the asymptotic intensity at infinite glucose (minus the signal at zero concentration, "a"), and "c" gives the glucose concentration at which the intensity is one-half the difference between the asymptotic value and the background, i.e. a+b/2. The "c" parameter is thus analogous to the Michaelis-Menten constant, $K_m$, in enzyme kinetic systems as described previously.

Figure 13:
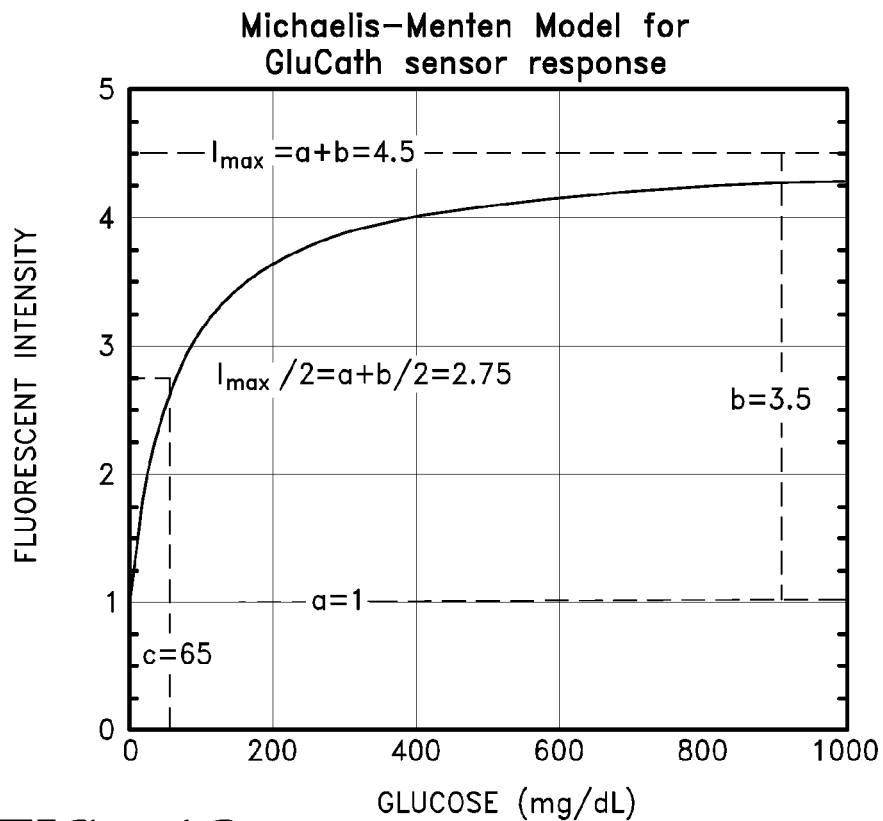
FIG. 13 displays a GluCath Calibration Curve with Michaelis-Menten Parameters.

In FIG. 13 above, the value of the "a" parameter is 1, meaning that the fluorescent intensity at zero concentration of glucose is equal to 1 as shown on the graph. The value of the "b" parameter in FIG. 13 is 3.5, hence the asymptotic intensity at infinite or very high concentration of glucose plus the background, as shown, is equal to 4.5. Finally, the "c" parameter in the example shown is 65, and is equivalent to the concentration of the analyte, glucose, at one-half the asymptotic intensity minus the background which is 2.75.

It should be noted that for certain embodiments of the glucose sensing chemistry, as with some other chemical systems conforming to Michaelis-Menten kinetics, the value of the Michaelis-Menten constant, $K_m$, or the "c" parameter is a substantially fixed property of the chemistry. In the case of the GluCath sensor, the "c" parameter is determined by the binding constant between glucose and the Receptor-Quencher.

Given the values of the Michaelis-Menten parameters, the Michaelis-Menten equation can be inverted or solved for glucose (G):

$$G=c*(I-a)/(a+b-I)$$

Calibration of the GluCath sensor consists of establishing the values of the Michaelis-Menten parameters and inserting them into the glucose equation above.

Other Equations Fitting the Response Curve

One method of calibrating the GluCath sensor is based on use of the Michaelis-Menten equation as described herein. The Michaelis-Menten equation is also useful for calibrating glucose sensors based on other sensing mechanisms such as, for example, glucose sensors based on lifetime chemistry as described below. Furthermore, the Michaelis-Menten equation may also be useful for calibrating sensors designed to measure concentrations of analytes other than glucose. However, it should be noted that many equations representing the form of a rectangular hyperbola may be used to fit the binding curve of the GluCath system as well as the binding curves of other analyte sensors disclosed herein.

The following discussion of rectangular hyperbolas is taken from Appendix A of Conners K. A. *Binding Constants: The Measurement of Molecular Complex Stability*, John Wiley & Sons, Inc., New York, 1987. A more thorough discussion, and the definition of terms, can be found in the original text.

The binding isotherm for a 1:1 stoichiometry has the form of Eq. (A.1), $$y=dx/(f+ex) \quad (A.1)$$

where d, e, f are parameters. Equation (A.2) is a more general expression of the same form, $$y=(c+dx)/(f+ex) \quad (A.2)$$

Equations A.1 and A.2 are the equations of a rectangular hyperbola.

Some experimental manifestations of Eq. A1 are the 1:1 binding isotherm (A.19), the fraction of weak acid HA in the conjugate acid form (A.20), the spectrophotometric measure of 1:1 binding (A.21), and the Michaelis-Menten equation of enzyme kinetics (A.22):

$$f_{11}=(K_{11}[L])/(1+K_{11}[L]) \quad (A.19)$$

$$F_{HA}=[H^+]/(K_a+[H^+]) \quad (A.20)$$

$$\Delta A/b=(K_{11}S_t\Delta\epsilon[L])/(1+K_{11}[L]) \quad (A.21)$$

$$v=V_m[S]/(K_m+[S]) \quad (A.22)$$

All of these equations can be rewritten in the reduced form of the rectangular hyperbola, Eq. (A.23), by defining the variables as in Table A.1

$$Y_r=X_r/(1+X_r) \quad (A.23)$$

TABLE A.1

Reduced forms of some experimental curves

| Usual form | Reduced form | $y_r$ | $x_r$ |
|---|---|---|---|
| Eq. (A.19) | $f_{11} = K_{11}[L]/(1 + K_{11}[L])$ | $f_{11}$ | $K_{11}[L]$ |
| Eq. (A.20) | $F_{HA} = \{(H^+)/K_a\}/\{1 + (H^+)/K_a\}$ | $F_{HA}$ | $(H^+)/K_a$ |
| Eq. (A.21) | $\Delta A/(S_t b\Delta\epsilon) = K_{11}[L])/(1 + K_{11}[L])$ | $\Delta A/(S_t b\Delta\epsilon)$ | $K_{11}[L]$ |
| Eq. (A.22) | $v/V_m = [S]/(1 + [S]/K_m)$ | $v/V_m$ | $[S]/K_m$ |

The GluCath binding mechanism can also be described by:

$$F=F_{min}+F_{max}K[G]/(1+K[G])$$

Where F is the GluCath fluorescence intensity as a function of glucose concentration, $F_{min}$ is the fluorescence intensity of the system with no glucose present, $F_{max}$ is the maximum intensity when the system is saturated with glucose, and K is the binding affinity of the receptor for glucose.

Methods of Calibration

Disclosed herein are methods for determining the appropriate values of the Michaelis-Menten parameters used to relate the fluorescent intensity measured by an analyte sensor to the analyte concentration surrounding the sensor. In certain such methods the analyte is glucose, and the glucose sensor is more particularly a GluCath sensor. In certain such methods, the Michaelis-Menten parameters are determined in reference to an analyte sensors based on lifetime chemistry. However, in the description of the methods that follows, reference will be made to a glucose sensor or more particularly a GluCath sensor. Nevertheless, it should be understood that the disclosed methods may be used to calibrate any analyte sensor which may be characterized by the Michaelis-Menten equation or a modified form of the Michaelis-Menten equation.

Methods described below involve a combination of experimental measurement and numerical calculation to establish the appropriate values of the Michaelis-Menten parameters describing the sensor response to glucose. As in many chemical systems, the response of the GluCath sensor chemistry is sensitive to other chemical parameters in addition to the analyte of interest. For example, the GluCath sensor is often sensitive to variations in both pH and temperature, hence in the experimental determination of the sensor response, both the pH and temperature should be held at or near to their physiological values (e.g., 7.4 and 37 degree centigrade). Alternatively, the experimental determination of the sensor response can be obtained at other values of pH and temperature, provided that the effect of pH and temperature on the intensity response curve has been separately characterized.

In a first method, Method 1, the Michaelis-Menten parameters are determined from a set of in vitro measurements of the fluorescent intensity using three or more solutions of known glucose concentrations. Method 1 could use, for example, three sterile calibration solutions at precisely determined glucose concentrations, e.g., 0, 400 and 100 mg/dL glucose, respectively. Method 1 could also use, equivalently, three other values of glucose determined by an appropriate independent laboratory measurement. In certain such methods, it is advantageous that the solutions be held at or near physiological pH and temperature (7.4 and 37 degree centigrade). The sensor is inserted into a test chamber and exposed to the three glucose concentrations. The fluorescent intensity is recorded for each of the glucose concentrations and the resulting data can be used to analytically determine the corresponding Michaelis-Menten parameters. Alternatively or in addition, the corresponding Michaelis-Menten parameters may be determined numerically from the resulting data using the method of least squares.

The analytic solution for a set of three pre-established or independently-determined glucose values (G1, G2, G3) and three corresponding values of the fluorescent intensity (I1, I2, I3) are given below. The first parameter to be determined is the "c" parameter (c0):

$$c_0[-G_1*G_2*(I_1-I_2)+G_1*G_3*(I_3-I_1)+G_2*G_3*(I_2-I_3)]/[G_1*(I_3-I_2)+G_3*(I_2-I_1)+G_2*(I_1-I_3)]$$

Once the value of the "c" parameter has been determined, $c_0$, it can be used to find the value of the "b" parameter, $b_0$:

$$b_0=(I_1-I_2)/[(G_1/(c_0+G_2/(c_0+G_2)]$$

Finally, the value of the "a" parameter, $a_0$, can then be determined from the intensity measurements ($I_1$, $I_2$, $I_3$), the corresponding glucose values ($G_1$, $G_2$, $G_3$) and the values obtained above for $c_0$ and $b_0$:

$$a_0=I_1-(b_0+G_1)/(c_0+G_1)$$

The values for the Michaelis-Menten parameters ($a_0$, $b_0$, $c_0$) can then be substituted into the inverted Michaelis-Menten equation to give the glucose value G corresponding to any measured fluorescent intensity, I:

$$G=c_0*(I-a_0)/(a_0+b_0-I)$$

This equation thus converts a measured fluorescent intensity, I, into a glucose value, G. It can be used in both in vitro and in vivo applications under the assumption that the fluorescent intensity does not change substantially (for a given glucose concentration) between the determination of the Michaelis-Menten parameters and the experimental application.

Figure 14:
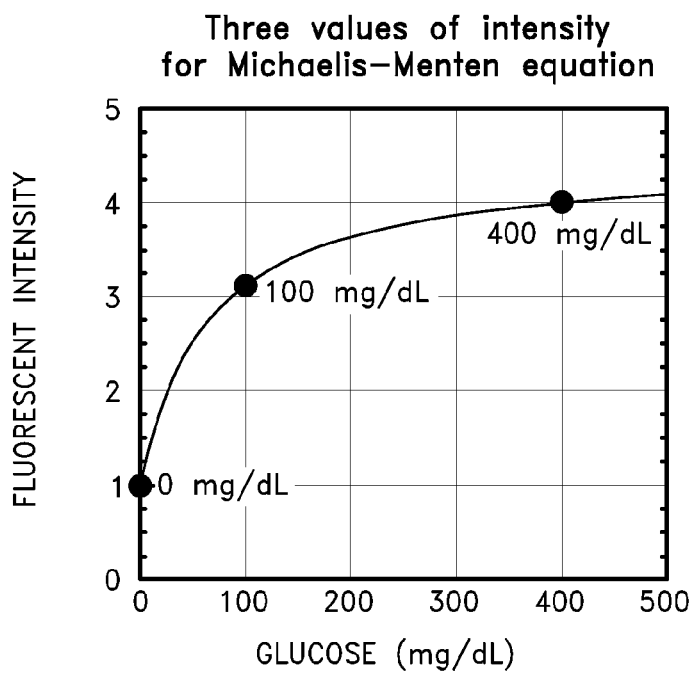
FIG. 14 displays a GluCath Calibration Curve with measurement at three values of the analyte.

FIG. 14 gives an example of the Michaelis-Menten response with corresponding measurements of the fluorescent intensity and the analyte concentration at three distinct values. In the example shown, these values are 0, 100 and 400 mg/dL.

As mentioned above, the values of the Michaelis-Menten parameters ($a_0$, $b_0$, $c_0$) may be computed numerically from a set of measured pairs of fluorescent intensities and analyte concentrations instead of analytically using the three equations described above. For example, in some embodiments, the parameters are computed numerically using the method of least squares. However, in principle, any numerical method appropriate for fitting an equation linear in three variables to a set of points may be used to determine appropriate values for the Michaelis-Menten parameters ($a_0$, $b_0$, $c_0$). Moreover, numerical methods may be employed to compute best fit values of $a_0$, $b_0$, and $c_0$ on a dataset comprising more than three pairs of fluorescent intensities and analyte concentrations. For example, if the fluorescent intensity is measured for 4 standard solutions of differing known analyte concentrations, various numerical methods, such as linear least squares, may be used to compute best fit values of the Michaelis-Menten parameters ($a_0$, $b_0$, $c_0$). In principle, and depending on the embodiment, the more standards solutions that are used, the more reliable the parameters may be determined.

In a second method, Method 2, an additional calibration step is used to compensate for changes in the fluorescent intensity that occur between the determination of the Michaelis-Menten parameters and the use of the sensor in an in vitro or in vivo application. In Method 2, an additional measurement is made of the fluorescent intensity of the sensor after placement in the in vitro or in vivo environment. A simultaneous and independent measurement is also be made of the concentration of the analyte (e.g. glucose) at this time. In the case of glucose, the independent measurement of the analyte concentration could be made with an approved handheld device, such as a point-of-care glucometer, or it could be made with a laboratory reference device such as a blood gas analyzer. The measured value of the analyte, $G_0$, is then used in conjunction with the previously determined values of the Michaelis-Menten parameters ($a_0$, $b_0$ and $c_0$) to give a predicted fluorescent intensity $I_{pred}$ at the value of analyte according to the Michaelis-Menten equation:

$$I_{pred}=a_0+b_0*G_0/(c_0+G_0)$$

The predicted fluorescent intensity ($I_{pred}$) can then be compared with the measured fluorescent intensity $I_{meas}$ which was obtained experimentally. In Method 2, a correction factor, $C_F$, is determined from the ratio of the measured and the predicted fluorescent intensity at the particular value of the analyte ($G_0$):

$$C_F=I_{meas}(G_0)/I_{pred}(G_0)$$

The correction factor, $C_F$, can then be used to provide an adjustment of the Michaelis-Menten "a" and "b" parameters to optimize the agreement between the measured fluorescent intensity and the fluorescent intensity predicted by the calibration equation at the value of the analyte $G_0$:

$$I_{meas} = I_{pred}$$
$$= C_F * a_0 + C_F * b_0 * G_0/(c+G_0)$$

Method 2 provides a multiplicative correction to the value of the original set of Michaelis-Menten parameters based on the simultaneous measurement of the fluorescent intensity and the actual value of the analyte concentration or glucose. It results in a new set of values in the Michaelis-Menten equation for the "a" and "b" parameters:

$$a'=C_F*a_0$$

$$b'=C_F*b_0$$

In Method 2, only the "a" and "b" parameters of the Michaelis-Menten equation are changed. As noted previously, the Michaelis-Menten "c" parameter which is in large part determined by the binding constant between the quencher-receptor and glucose remains unchanged. The final calibration equation is given by:

$$G=c_0*(I-a')/(a'+b'-I)$$

where $c_0$ is the original value of the Michaelis-Menten "c" parameter, and a' and b' are the values determined by the one-point in vivo adjustment described above using Method 2. This is shown graphically in FIG. 15 below where the difference in the measured fluorescent intensity and the predicted fluorescent intensity at 130 mg/dL is used to calculate the correction factor $C_F$ from which the values of the new "a" and "b" parameters can be obtained according to Method 2. In the example shown in FIG. 15, the correction factor $C_F$ is 1.2, making a' equal to 1.2 and b' equal to 4.2.

The third method, Method 3, also begins with an initial set of Michaelis-Menten equation parameters computed either analytically or numerically as described with respect to Method 1. As in Method 2, an additional calibration step is also required to compensate for changes in the fluorescent intensity that occur between the determination of the Michaelis-Menten parameters and the use of the sensor in an in vitro or in vivo application. This step in Method 3 is different mathematically than the step used in Method 2. As in Method 2, an additional measurement is required of the fluorescent intensity of the sensor after placement in the in vitro or in vivo environment. A simultaneous and independent measurement must also be made of the concentration of the analyte (e.g. glucose) at this time. As in Method 2, the predicted fluorescent intensity ($I_{pred}$) can then be compared with the measured fluorescent intensity $I_{meas}$ which was obtained experimentally. The measured value of the analyte, $G_0$, is then used in conjunction with the previously determined values of the Michaelis-Menten parameters ($a_0$, $b_0$ and $c_0$) to give a predicted fluorescent intensity $I_{pred}$ at the value of analyte according to the Michaelis-Menten equation:

$$I_{pred}=a_0+b_0*G_0/(c_0+G_0)$$

In Method 3, however, an additive correction factor, CA, is determined from the difference between the measured and the predicted fluorescent intensity at the particular value of the analyte (G0):

$$C_A=I_{meas}-I_{pred}$$

This gives a new equation for the intensity $$\begin{aligned}I &= C_A + I_{pred}\\ &= C_A + a_0 + b_0 * G_0/(c_0 + G_0)\\ &= a' + b_0 * G_0/(c_0 + G_0)\end{aligned}$$

where the new value of the "a" parameter, a', is given by $a'=a_0+C_A$

Figure 16:
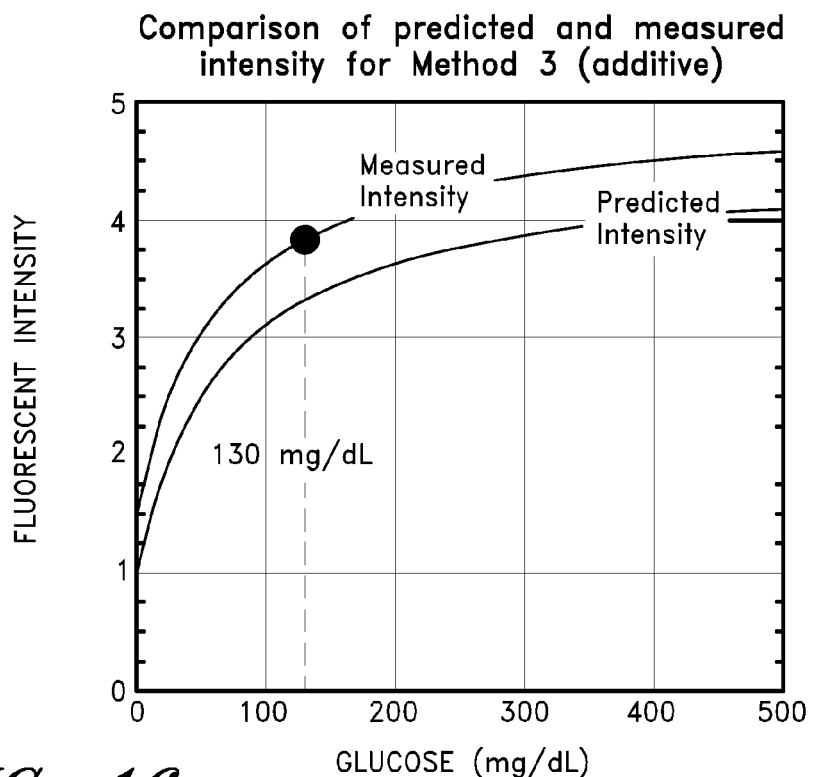
FIG. 16 displays a comparison of predicted and measured intensity used in one-point in vivo adjustment of the Michaelis-Menten parameters according to Method 3 disclosed herein with an additive correction factor $C_A$.

FIG. 16 below shows the correction of the Michaelis-Menten equation using Method 3 and the additive correction associated with it. In the example shown, the measured background fluorescence has increased by 50% but the Michaelis-Menten "b" and "c" parameters have been unaffected. In Method 3, the one-point in vivo adjustment has been used to modify the calibration curve to reflect the change in the background fluorescence.

In one embodiment, the values of the Michaelis-Menten equation parameters can be determined by Methods 1, 2, or 3 using prefilled sterile calibration solutions at specified values such as 0, 100 and 400 mg/dL. This calibration could, in principle, be done at the bedside of a patient immediately before insertion of the sensor into a vein or artery. The calibration solutions can be produced at an equivalent physiological pH level such as 7.4. A temperature control feedback loop can be used to maintain the calibration solutions at an equivalent stable physiological temperature for the duration of the calibration procedure.

In the fourth method, Method 4, the initial values of the Michaelis-Menten equation parameters are determined by the manufacturer or vendor, for example in a laboratory at the factory during manufacturing or prior to packaging, instead of by the end user or consumer, for example by a clinician at the patient's bedside. In this case, the Michaelis-Menten parameters can be determined from a multipoint in situ calibration in which, again, both the pH and temperature are carefully controlled. The initial determination of the Michaelis-Menten parameter values can thus be regarded as a factory calibration. In some embodiments, 4, 5, 6, 7, 8, 9, 10 or more standard calibration solutions of known analyte concentration may be used in a factory calibration, and the Michaelis-Menten parameters may be determined by numerical methods. In other embodiments, a factory calibration employing 3 standard calibration solutions may be sufficient.

Figure 17:
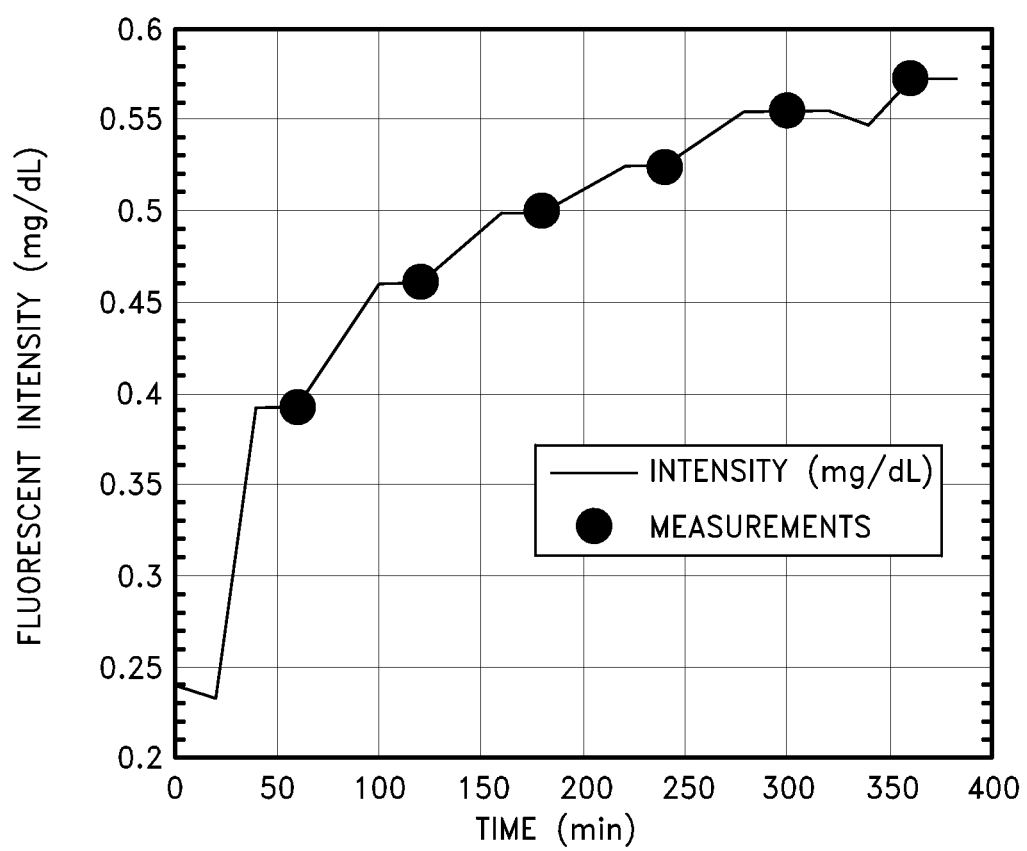
FIG. 17 displays hypothetical data from a laboratory characterization of GluCath sensor response.

The calibration can be carried out using calibration solutions with a glucose concentration of 0 to 600 mg/dL at 10 to 60° C. with a calibration time of 0 to 360 minutes. More preferably, the calibration solutions will have a glucose concentration of 0 to 400 gm/dL at 30 to 50° C. with a calibration time of 10 to 360 minutes. In one preferred embodiment, the calibration comprises exposing the chemical indicator system to a 100 mg/dL calibration solution at 42° C. for 90 minutes, followed by exposing the chemical indicator system to a 100 mg/dL calibration solution at 33° C. for 120 minutes. In other embodiments, the calibration comprises multiple cycles comprising different calibration solutions with different analyte concentrations and/or temperature and/or exposure time. FIG. 17 below shows a hypothetical data set from a typical laboratory characterization of the GluCath sensor response to glucose. Over a period of six hours, for example, a series of fluorescent intensity measurements were made using a GluCath sensor at six distinct glucose levels (50, 100, 150, 200, 300 and 400 mg/dL). The time, the measured fluorescent intensity, and the independently determined glucose concentration are given in Table 2. In other embodiments, the series of fluorescent intensity measurements are made over a shorter period, for example 10 to 30 minutes.

TABLE 2

Example In Situ Factory Calibration Test Data

| TIME (minutes) | GLUCOSE (mg/dL) | FLUORESCENT INTENSITY (volts) |
|---|---|---|
| 60 | 50 | 0.39267 |
| 120 | 100 | 0.46099 |
| 180 | 150 | 0.49974 |
| 240 | 200 | 0.52470 |
| 300 | 300 | 0.55496 |
| 360 | 400 | 0.57264 |

The data shown in Table 2 above can be used to determine the values of the Michaelis-Menten parameters required for the first step in the factory calibration. This results in an initial calibration equation from the factory calibration with the following parameters:

$$G=c_{FC}*(I-a_{FC})/(a_{FC}+b_{FC}-I)$$

where $a_{FC}$ is the factory calibrated value of the Michaelis-Menten "a" parameter, $b_{FC}$ is the factory calibrated value of the Michaelis-Menten "b" parameter and $c_{FC}$ is the factory calibrated value of the Michaelis-Menten "c" parameter. In the example shown here, the values of the parameters from the factory calibration are the following:

$$a_{FC}=0.24$$

$$b_{FC}=0.4$$

$$c_{FC}=81.0$$

In Method 4, the factory calibration giving the initial Michaelis-Menten parameter values is then combined with the multiplicative method (Method 2) discussed above. This calibration is in essence a factory calibration with a one-point in vivo adjustment using the correction factor, $C_F$, or the multiplicative method (Method 2) to bring the measured and predicted fluorescent intensities into agreement with one another. A final set of Michaelis-Menten Menten equation parameters are generating which result in a calibration equation, as described earlier, that converts a measured fluorescent intensity into a glucose value:

$$G=c_{FC}*(I-a_{FC}')/(a_{FC}'+b_{FC}'-I)$$

where the Michaelis-Menten "$c_{FC}$" parameter was determined entirely by the factory calibration (e.g., $c_{FC}$=81.0) and the Michaelis-Menten $a_{FC}'$ and $b_{FC}'$ parameters were determined by the one-point in vivo adjustment applied to the original factory calibration parameters.

In Method 5, the same factory calibration procedure is used as in Method 4 above, but the one-point in vivo adjustment using the additive correction factor, $C_A$, (described in Method 3 above) changes only the Michaelis-Menten "a" parameter. The resulting calibration equation giving the glucose as a function of measured fluorescent intensity is the following:

$$G=c_{FC}*(I-a_{FC}')/(a_{FC}'+b_{FC}-I)$$

where the values of the Michaelis-Menten $b_{FC}$ and $c_{FC}$ parameters were determined entirely by the factory calibration (e.g., $b_{FC}$=0.40 and $c_{FC}$=81.0) and the Michaelis-Menten $a_{FC}'$ parameter only was changed by the one-point in vivo adjustment applied to the original factory calibration parameters.

In Method 6, the same procedure is used to obtain the factory calibration parameters but the one-point adjustment is applied twice: first in vitro, for example, in a sterile prefilled calibration solution at the patient's bedside and second in vivo with an independent measurement of the patient's blood glucose. In both the in vitro and in vivo adjustment, the change in the parameters is applied to both $a_{FC}$ and $b_{FC}$ using the correction factor or multiplicative method (described in Method 2 above).

In Method 7, the same procedure is used as in Method 6 together with both an in vitro one-point adjustment and an in vivo one-point adjustment, but the change is applied only to $a_{FC}$ using the additive correction factor or additive method (described in Method 3 above).

Method 8 differs slightly from the methods described above in that it uses the factory calibration for a determination of the Michaelis-Menten "c" parameter, ($c_{FC}$) and for an initial determination of the Michaelis-Menten "a" and "b" parameters ($a_{FC}$ and $b_{FC}$), but it also uses a two-point in vivo calibration at two distinct glucose levels (G1 and G2) measured in the patient. Since the value of the "c" parameter is determined in the factory calibration procedure $c_{FC}$, it can be used to find the value of the "b" parameter ($b_0$) using the two-point in vivo calibration measurement with glucose values $G_1$ and $G_2$ and fluorescent intensity values $I_1$ and $I_2$:

$$b_0=(I_1-I_2)/[(G_1/(c_{FC}+G_1)-G_2/(c_{FC}+G_2)]$$

Finally, the value of the "a" parameter, $a_0$, can then be determined from one of the intensity measurements ($I_1$, $I_2$,), one of the corresponding glucose values ($G_1$, $G_2$), and the values obtained above for $c_{FC}$ and $b_0$:

$$a_0=I_1-(b_0+G_1)/(c_{FC}+G_1)$$

This results, again, in a calibration equation based on the inverted Michaelis-Menten equation which gives glucose as a function of the measured intensity of the GluCath sensor system:

$$G=c_{FC}*(I-a_0)/(a_0+b_0-I)$$

Figure 18:
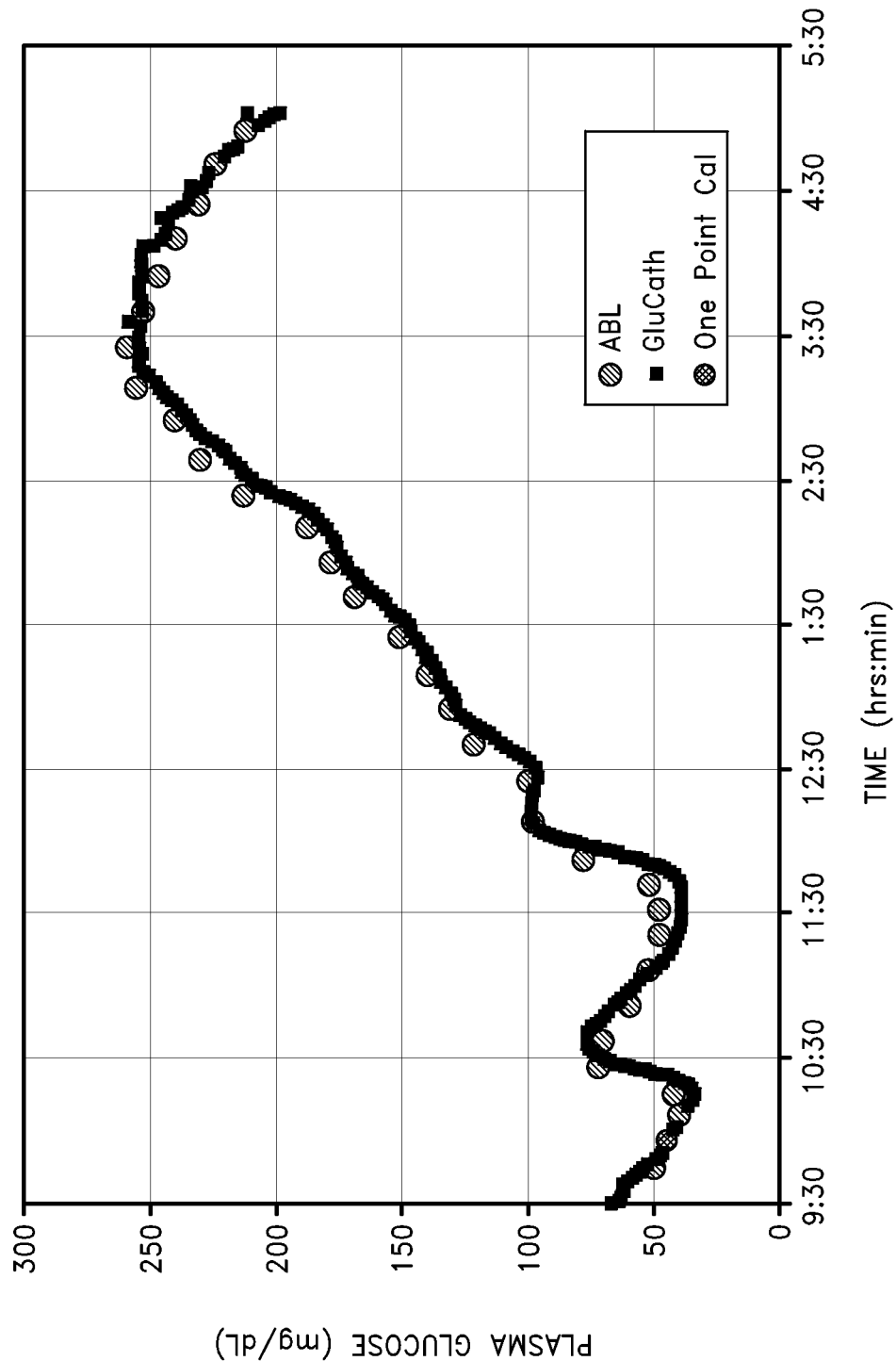
FIG. 18 displays a comparison of the GluCath sensor from a human clinical study calibrated with Method 5 disclosed herein and compared with blood gas analyzer glucose values using an ABL Radiometer

In summary, all of the methods described above, provide values of the Michaelis-Menten equation parameters derived in one way or another in order to generate a calibration equation. These methods have been tested in laboratory in vitro experiments, in pre-clinical in vivo experiments in a suitable animal model, and in clinical in vivo studies with human volunteer subjects with type 1 diabetes. FIG. 18 below shows the high level of agreement between the GluCath sensor from a human clinical study with a type 1 diabetic subject using the calibration method described above and venous sample glucose measurements made with an ABL Radiometer blood gas analyzer. The calibration method used here was Method 5, the same factory calibration procedure with a one-point in vivo adjustment using the additive correction factor, CA, Finally, it is noted that in some embodiments, Michaelis-Menten parameters determined for one manufactured sensor can be successfully used with another manufactured sensor to provide sufficiently accurate results. For example, if two sensors are designed similarly, and/or manufactured similarly, and/or manufactured to the same specifications, independent calibration of the two sensors may yield nearly identical (or very similar) values for the Michaelis-Menten parameters. Accordingly, it may be efficient, cost effective, and sufficiently accurate to employ one set of Michaelis-Menten parameters for both sensors. Alternatively, a set of Michaelis-Menten parameters for an entire manufactured batch of sensors may be determined by calibrating a select few of the sensors, and averaging the resulting values to obtain a set of Michaelis-Menten parameters for the batch.

Implementation into an Analyte Monitoring System

In some embodiments, an analyte sensor can be functionally connected to an analyte monitor. In various embodiments, the analyte monitor can convert fluorescence readings to analyte measurements, display analyte readings, transmit analyte readings, store analyte readings, compare analyte readings, or some combination of these functions. Keyboard or data entry subsystems can be functionally attached to or integrated into a monitor. Various parts can be interconnected by wire, cable, and/or wireless connections, and involve electrical, optical, radio signals, or other appropriate techniques.

The monitor can utilize one or more values of the calibration parameters, including the Michaelis-Menten parameters (a, b and c), and the correction factors $C_A$ and $C_F$. In some embodiments, values of calibration parameters can be preloaded into the monitor, such as by storing one or more value in memory, whether by the user or another party. In some embodiments, one or more values of the calibration parameters can be entered after following a calibration procedure, either with the analyte sensor functionally connected to the monitor or with the analyte sensor connected to a different monitor or reading device. In some embodiments, when a different monitor or reading device is used for calibration, information relating to the calibration can be communicated directly or indirectly between the monitor and the different monitor or reading device functionally connected to the analyte sensor during calibration. In some embodiments, the monitor will receive information relating to the measurement of analyte concentrations as determined with a different device or by a different technique, and use the information during calibration. In some instances, the information can be sent to the monitor with manual entry, such as by keyboard or touchscreen or other manual methods; or by direct or indirect communication with a separate device determining the analyte concentration; or by reading values from an information storage medium such as scanning written or printed information, scanning barcodes, reading magnetic, optical, or computer storage medium including disks, strips, RAM, flash drives, etc.

In some embodiments, the calibration can be performed with purchased or prepared standards, including those with known concentrations of analyte or causing a response by the analyte sensor that is correlatable to analyte levels. In some embodiments, the purchased or prepared standard can include information, such as recorded on a tag, label, inclosure, etc. that is read by the monitor or a device functionally connected to the monitor.

In some embodiments, a monitor can have multiple sets of calibration values stored in memory. Different values can be associated with different sensors, different classes of sensors, different types of sensors, different types of displays, and different types of analyte reading correlation, such as to correlate with a particular brand of analyzer or for analysis performed by a particular methodology. Transition between different calibration values can be by switch, soft switch, jumper, secure connector, or other appropriate techniques. Security protocols and/or access limiting techniques can be utilized to prevent inadvertent or an authorized changing of calibration values.

In some embodiments, the monitor can be a dedicated monitor, such as for a single sensor for a single analyte determination. In some embodiments, the monitor can be a multiuse device which includes other patient monitoring and/or data storage functions, or the analyte monitoring function can be integrated into a patient monitoring system used for monitoring other conditions.

In some embodiments, a monitor can include a computer or microprocessor adapted for use with fluorometric analyte measurements with software or firmware capable of utilizing a three parameter analyte level determination as in the modified Michaelis-Menten equation as a part of a determination of analyte levels, or, in addition, utilizing correction factors to determine analyte levels, as described above. In some embodiments, a monitor capable of determining the values of these parameters can be utilized.

In some embodiments, the monitoring system can be integrated into a network including other devices such as additional monitors, displays including remote displays, televisions, data entry locations, computers, PDAs, telephones, monitoring stations, doctor offices, hospitals, etc. Networking can be via the Internet, local area network, wide-area network, secure network, private network, etc.

Use with Particular Types of Analyte Sensors

In some embodiments, the calibration techniques and methods described herein may be utilized with fluorescence-based analyte sensors, such as those having a chemical indicator system comprising a fluorophore functionally connected to an amine and a derivative of boronic, arsenious, or germanic acid (including derivatives of their salts) and those having a fluorophore functionally connected to a derivative of boronic, arsenious, or germanic acid (including derivatives of their salts), as described above. In particular embodiments, a fluorescence-based analyte sensor can have a chemical indicator system comprising a fluorophore that exists in at least two different forms depending on the concentration of a second analyte, such as where these two different forms of the fluorophore fluoresce at different wavelengths. The chemical indicator system of the sensor can also include a binding moiety that binds a first analyte, and the binding moiety can be operably coupled to the fluorophore and causes an optical change in the apparent concentration of the fluorophore related to concentration of the first analyte. The fluorophore can be a fluorescent dye and it can be a fluorescent dye that is a discrete compound or part of a larger molecule. Exemplary materials that can be used as the fluorophore of the chemical indicator system include HPTS-CysMA and HPTS-LysMA. In one embodiment, the binding moiety comprises a quencher, which can change or eliminate fluorescence from a fluorescent dye, in a binding region which can reversibly bind the first analyte. Exemplary materials that can be used as the analyte binding moiety of the chemical indicator system include viologen, compounds comprising a benzylboronic acid group, and compounds comprising a viologen-boronic acid adduct. In another embodiment, the binding moiety includes 3,3'-oBBV and derivatives thereof. Embodiments include those fluorescence-based sensors able to measure glucose levels in fluids including blood. Suitable sensors include those described in co-pending U.S. patent application Ser. Nos. 11/671,880, 12/027,158 and 12/612,602; each of which is incorporated herein in its entirety by reference thereto.

In some embodiments, the calibration techniques and methods described herein may be utilized with analyte sensors based on lifetime chemistry as described above.

Calibration Accuracy

In some embodiments, the objective of a calibration can be to linearize the signal readings in relation to the analyte levels, with far less emphasis on obtaining analyte measurements that are deemed "correct" or in agreement with other analyses. Linearization alone can be of use in various situations including those where relative values over time are of interest as well as for other reasons.

In some embodiments, the objective of the calibration can be to determine the actual value of an analyte concentration or to obtain analyte level measurements that are in agreement with measurements taken by another sensor, method, or instrument. In some preferred embodiments, the objective of the calibration can be to linearize the readings, i.e. convert the readings to a form that more closely approximates a line when plotted against the concentration of analyte present or determined as present, and to relate them to readings from other instruments or techniques that can be linearized also. In some preferred embodiments, the readings may be linearized or are linearizable over a particular range. One way to gauge the agreement between the measurements taken by different sensors, methods, or instruments (or the measurement and a value accepted as correct) is to determine the percentage difference between the readings (or reading and value), which is the difference between the two readings (or the reading and the value) divided by their average.

In some embodiments, the agreement or accuracy is more desirable for readings within a particular range than for readings outside of that range. For physiological parameters, a desirable range for readings can be described as a region around a normal reading for the parameter, although what is "normal" will tend to vary somewhat between individuals, situations, and with time. While a calibration for an analyte sensor can be performed over a very broad range, a calibration can also be performed over a more limited range such as by selecting standard calibration solutions that are within about 5%, 10%, 25%, 50%, 100%, 200%, 400%, or about 600% of a normal or target value.

Glycemic Control—Van Den Berghe Studies

A specific type of polyneuropathy develops in patients that are treated within an intensive care unit (hereinafter also designated ICU) for several days to weeks and this for a variety of primary injuries or illnesses. This polyneuropathy, known as "Critical Illness Polyneuropathy" (hereinafter also designated CIPNP) occurs in about 70% of patients who have the systemic inflammatory response syndrome (SIRS) (Zochodne D W et al. 1987 Polyneuropathy associated with critical illness: a complication of sepsis and multiple organ failure. Brain, 110: 819-842); (Leijten FSS & De Weerdt A W 1994 Critical illness polyneuropathy: a review of the literature, definition and pathophysiology. Clinical Neurology and Neurosurgery, 96: 10-19). However, clinical signs are often absent and it remains an occult problem in many ICUs worldwide. Nonetheless, it is an important clinical entity as it is a frequent cause of difficulty to wean patients from the ventilator and it leads to problems with rehabilitation after the acute illness has been treated and cured.

When CIPNP is severe enough, it causes limb weakness and reduced tendon reflexes. Sensory impairment follows but is difficult to test in ICU patients. Electro-physiological examination (EMG) is necessary to establish the diagnosis (Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495). This examination will reveal a primary axonal degeneration of first motor and then sensory fibers. Phrenic nerves are often involved. Acute and chronic denervation has been confirmed in muscle biopsies of this condition. If the underlying condition (sepsis or SIRS) can be successfully treated, recovery from and/or prevention of the CIPNP can be expected. This will occur in a matter of weeks in mild cases and in months in more severe cases. In other words, the presence of CIPNP can delay the weaning and rehabilitation for weeks or months.

The pathophysiology of this type of neuropathy remains unknown (Bolton C F 1996 Sepsis and the systemic inflammatory response syndrome: neuromuscular manifestations. Crit. Care Med. 24: 1408-1416). It has been speculated to be directly related to sepsis and its mediators. Indeed, cytokines released in sepsis have histamine-like properties which may increase microvascular permeability. The resulting endoneural edema could induce hypoxia, resulting in severe energy deficits and hereby primary axonal degeneration. Alternatively, it has been suggested that cytokines may have a direct cytotoxic effect on the neurons. Contributing factors to disturbed microcirculation are the use of neuromuscular blocking agents and steroids. Moreover, a role for aminoglucosides in inducing toxicity and CIPNP has been suggested. However, there is still no statistical proof for any of these mechanisms in being a true causal factor in the pathogenesis of CIPNP.

Although polyneuropathy of critical illness was first described in 1985 by three different investigators, one Canadian, one American, and one French, to date there is no effective treatment to prevent or stop Critical Illness Polyneuropathy.

To date the current standard of practice of care, especially of critically ill patients, was that within the settings of good clinical ICU practice, blood glucose levels are allowed to increase as high as to 250 mg/dL or there above. The reason for this permissive attitude is the thought that high levels of blood glucose are part of the adaptive stress responses, and thus do not require treatment unless extremely elevated (Mizock B A. Am J Med 1995; 98: 75-84). Also, relative hypoglycemia during stress is thought to be potentially deleterious for the immune system and for healing (Mizock B A. Am J Med 1995; 98: 75-84).

In a prospective clinical study, Van Den Berghe (US 2002/0107178) tested the hypothesis that the incidence of CIPNP can be reduced by more strict metabolic using intensive insulin treatment from admission onward. Between Feb. 2 and Apr. 25, 2000, 400 patients were included in the study. They had been randomly allocated to one of two insulin (Actrapid H M NovoLet of Novo Nordisk) treatment schedules:

(1) insulin infusion started at a dose of 1 U/h only when blood glucose is >230 mg/dL (13 mmol/L) and titrated up (2 to 4 hourly controls of blood glucose levels) with increments of 0.5 to 1 U/h to keep blood glucose below this level [180-200 mg/dL (10.3-11.2 mmol/L)]. When blood glucose levels reach 180 mg/dL, insulin infusion is stopped.

(2) insulin infusion started when blood glucose is >120 mg/dL (6.8 mmol/L) at a dose of 2 U/h and titrated up (2 to 4 hourly controls of blood glucose levels) with increments adequate to keep blood glucose levels normal and thus below this level [80-110 mg/dL (4.6-6.1 mmol/L)]. Maximal hourly insulin dose is set at 60 Upper hour. When blood glucose levels reach 80 mg/dL, insulin infusion is tapered and eventually stopped until normal levels are again reached. During interruption of enteral tube feeding for determination of residual stomach content, insulin infusion is reduced proportionately to the reduction of caloric intake.

(3) Concomitantly, patients were fed, on the admission day using a 20% glucose infusion and from day 2 onward by using a standardized feeding schedule consisting of normal caloric intake (25-35 Calories/kgBW/24 h) and balanced composition (20%-40% of the non-protein Calories as lipids & 1-2 g/kgBW/24 h protein) of either total parenteral, combined parenteral/enteral or full enteral feeding, the route of administration of feeding depending on assessment of feasibility of early enteral feeding by the attending physician. All other treatments, including feeding regimens, were according to standing orders currently applied within the ICU.

Exclusion criteria were age <18y, pregnancy and not being intubated at admission.

When patients were still treated in the ICU after 7 days, a weekly EMG examination was performed to screen for the presence of CIPNP. The EMGs were always interpreted by the same expert in electrophysiology. In order to accurately assess ICU stay, which is often determined by other factors than the patient's condition—e.g. bed availability on the wards—"end of ICU stay" was defined as the day on which the attending physician considers the patient to be "ready for discharge".

A total of 83 patients ended up being treated on the ICU for at least one week and were screened by EMG for the presence of CIPNP. In the group randomized into the "intensive insulin schedule", 38 patients stayed for more than 7 days and in the group randomised into the "restrictive insulin schedule", 45 patients stayed more than 7 days. Fifteen out of 38 long-stay ICU patients in the intensive insulin group (or 39% of the long stayers) revealed a positive EMG for CIPNP at any time during the ICU stay versus 30 out of 45 in the restrictive insulin group (or 67%) ($P=0.01$ with Chi-square). In the intensive insulin group, the mean±SD number of positive EMGs for CIPNP per patient was 0.9±1.8 (median of zero) versus 1.8±2.1 (median of 1) in the restrictive insulin group ($P=0.015$ with Mann-Whitney U test).

Long-stay patients in the intensive insulin group had a CIPNP-free time on the ICU of 2.1±1.8 weeks versus 1.1±1.2 weeks in the restrictive insulin group ($P=0.004$ with unpaired Student's t-test).

ICU-mortality was not detectably different between the two treatment groups ($P=0.4$).

Van Den Berghe concluded that the study revealed that strict metabolic control with intensive insulin treatment and clamping of blood glucose levels within normal limits significantly reduces the incidence of CIPNP and lengthens the time free of CIPNP in patients that do develop this problem. This was the first study to point to a preventive strategy for this frequently occurring and important problem in ICU patients. Since the presence of EMG-proven CIPNP has been shown to extend the need for ICU support and to prolong the time required for rehabilitation, this treatment will lead to a reduction in need for ICU support and to a shorter time for rehabilitation, which could reflect a major reduction in costs.

Van Den Berghe also conducted a prospective, randomized, controlled study. All mechanically ventilated, adult patients admitted to the intensive care unit (ICU) were eligible for inclusion. Only 5 patients participating in another trial and 9 who were moribund or DNR coded at ICU admission were excluded. At admission, patients were randomized to either strict normalization of glycemia (4.5-6.1 mmol/L) with continuously infused insulin during intensive care, the 'intensive insulin schedule' (IIS), or the currently used 'restrictive insulin schedule' (RIS), with insulin started when blood glucose exceeds 12 mmol/L in which case glycemia is clamped to 10-12 mmol/L. An interim safety analysis revealed a difference in mortality, and the study was ended for ethical reasons.

A total of 1548 patients were included, 765 in the IIS group, 783 in the RIS group, well matched at inclusion. IIS reduced ICU mortality by 43% (P=0.005) [63 deaths in the RIS group versus 35 in the IIS group; death odds ratio for IIS, corrected for all baseline univariate predictors of ICU death, was 0.52 (0.33-0.82), P=0.004] and hospital mortality by 34% (P=0.01). Mortality reduction occurred exclusively in long-stay ICU patients and was due to prevention of death from multiple organ failure with sepsis. IIS also reduced the incidence of blood stream infections, renal failure, anemia and critical illness polyneuropathy as well as the need for dialysis or hemofiltration, red cell transfusion, prolonged mechanical ventilatory support and intensive care. Further details of the clinical study are disclosed in US 2002/0107178; incorporated herein in its entirety by reference thereto.

According to Van Den Berghe, the data suggested that disturbances in glucose metabolism during critical illness are not "adaptive and beneficial" since strict metabolic control with exogenous insulin substantially reduces morbidity and mortality.

The primary outcome measure in the Van Den Berghe study was death from all causes during intensive care. Secondary outcome measures were in-hospital mortality, incidence of prolonged intensive care dependency and need for ICU re-admission, need for vital organ system support comprising mechanical ventilatory support, renal replacement therapy (continuous or intermittent hemofiltration or dialysis), inotropic or vasopressor support, incidence of critical illness polyneuropathy, the degree of inflammation, incidence of blood stream infections and use of antibiotics, transfusion requirements and incidence of hyperbilirubinemia. Furthermore, use of intensive care resources was analyzed by cumulative TISS scores. In order to accurately and objectively assess duration of ICU stay, which is often influenced by non-patient related factors such as bed availability on regular wards, patients were defined 'dischargable from ICU' when they were no longer in need of vital organ system support and received at least ⅔rd of the caloric need through the normal enteral route or earlier when actually sent to a ward.

Van Den Berghe reported another study involving 1548 patients, 783 in the RIS group and 765 in the IIS group, well matched at randomization although IIS patients tended to be slightly older and more obese compared with RIS patients. A history of diabetes was present in 13.2% of patients, 4.6% treated with subcutaneous insulin injections, 8.6% receiving oral anti-diabetic treatment. On ICU admission, 74.6% of patients revealed glycemia higher than normal when compared with overnight fasted reference values (≥6.1 mmol/L) and 56% had a blood glucose level higher than the fasted diabetes threshold (≥7 mmol/L). Only 11.7%, however, revealed an on-admission glycemia in the non-fasting diabetes range (≥11 mmol/L). A non-fasting "diabetic" glycemia on ICU admission did not correlate well with having a history of diabetes, as only 19.6% of the known diabetics revealed a blood glucose level on ICU admission ≥11 mmol/L. The two study groups were comparable for diabetes diagnosed before ICU admission and for incidence of on-admission hyperglycemia.

Mean and maximal amount of non-protein Calories per patient (not including the first and last day of ICU stay) was 19±7 kCal/kg/24 h and 24±10 kCal/kg/24 h, respectively. Mean and maximal amount of dietary nitrogen was 0.14±0.06 gN/kg/24 h and 0.19±0.08 gN/kg/24 h, respectively. Daily amounts and composition of the feeding regimens were comparable in the two groups.

In the IIS group, 99% of patients required exogenous insulin, a need which persisted for the entire duration of ICU stay. Glycemia was well controlled with mean morning levels of 5.8±1.0 mmol/L. Only 0.1% of IIS patients had blood glucose levels that failed to go below 6.1 mmol/L within 48 h, 48% never exceeded 6.1 mmol/L after treatment initiation and only 17% occasionally peaked over 8.4 mmol/L. Mean morning glycemia in the RIS group was 8.5±1.8 mmol/L. Only 39% of RIS patients actually received insulin and those revealed a mean morning glycemia of 9.6±1.8 mmol/L in contrast to 7.8±1.4 mmol/L in the non-insulin requiring RIS patients.

In 39 IIS-treated patients, glycemia transiently fell below 2.3 mmol/L versus 6 patients in the RIS group. Such an event of hypoglycemia was always quickly corrected and never induced serious symptoms such as hemodynamic deterioration or epilepsia.

In the IIS group, 35 patients (4.6%) died during intensive care versus 63 (8.1%) in the RIS group (P=0.005), a relative risk reduction (RRR) of 43%. The "numbers needed to treat" (NNT) to save one life during intensive care was 29. The impact on ICU mortality by IIS was independent of the first 24 h-APACHE II and TISS scores. The intervention effect was also similar in patients after cardiac surgery and those suffering from other types of critical illness. ICU mortality among the RIS patients actually receiving insulin was 12.4% versus 5.2% among those not requiring insulin to keep glycemia below 12 mmol/L (P=0.0003).

Since it was hypothesized that a difference in mortality among long-stay ICU patients, Van Den Berghe's group sub-analyzed the effect in patients with an ICU stay of ≤5 days and in those staying >5 days. First 24 h-APACHE II score of patients staying ≤5 days was a median 9 (IQR 6-12) and 75% of them were patients after cardiac surgery. Median first 24 h-APACHE II in patients staying >5 days was 12 (8-15) and 68% were suffering from a non-cardiac surgery type of critical illness. The number of patients with an ICU stay of >5 days was not statistically different in the IIS (27%) and RIS (31%) groups (P 0.1). Mortality of patients staying ≤5 days was similar in IIS and RIS groups. Hence, the reduction in ICU mortality by IIS occurred selectively in the prolonged critically ill cohort with an absolute and relative risk reduction of 9.6% and 47%, respectively, and one life saved for every 11 treated long-stay patients.

All on-admission risk factors for ICU mortality were determined using univariate analysis. These comprised the first 24 h-APACHE II score, age, a non-cardiac surgery type of critical illness, tertiary referral, history of malignancy, and on-admission blood glucose level ≥11 mmol/L. These factors were subsequently entered into a multivariate logistic regression model together with the randomized insulin schedule. This revealed that the independent risk factors for mortality were the first 24 h-APACHE II score, age, a noncardiac surgery type of critical illness, tertiary referral and insulin treatment schedule. The death odds ratio for IIS, corrected for other baseline univariate predictors of ICU death, was 0.52 (95% confidence intervals 0.33-0.82). Analysis of the causes of death during intensive care revealed that IIS particularly reduced the risk of death from multiple organ failure with a proven septic focus on post-mortem examination.

IIS also significantly reduced total in-hospital mortality from 10.8% to 7.1% (P=0.01), a relative risk reduction of 34%. Again, this benefit was limited to the prolonged critically ill cohort.

IIS reduced duration of ICU stay whereas in-hospital stay was not detectably different between the two study groups. ICU re-admission rate was 2.1% and similar in both groups. In the IIS group, significantly less patients required prolonged mechanical ventilatory support and renal replacement therapy compared with the RIS group, whereas the need for inotropic or vasopressor support was identical. Independent of renal replacement therapy, kidney function parameters were more disturbed in the RIS group. The incidence of hyperbilirubinemia was significantly lower in the IIS group.

There was a 46% reduction in blood stream infections. Moreover, markers of inflammation were less disturbed and prolonged use of antibiotics (>10 days) less often required in the IIS group. The latter was largely attributable to the effect on bacteremia (75% of bacteremic patients were treated with antibiotics for >10 days versus 10% of non-bacteremic patients; P<0.0001). Mortality tended to be lower in bacteremic IIS patients (12.5%) compared with bacteremic RIS patients (29.5%; P=0.067). There was no difference between the two groups in the use of ICU drugs other than insulin or antibiotics.

Patients with an ICU stay of more than 1 week were screened weekly for critical illness polyneuropathy. Firstly, due to the effect on ICU stay, less IIS patients were screened. Secondly, among the screened patients in the IIS group, less revealed a positive EMG compared with the RIS group. Among screened patients, the NNT to prevent critical illness polyneuropathy in one patient was 4. Furthermore, critical illness polyneuropathy resolved more rapidly in the IIS group, as indicated by a lower fraction of patients with repetitive positive EMGs on the weekly screenings.

The use of aminoglycosides and glucocorticoids were determinants of critical illness polyneuropathy by univariate analysis. However, when entered into a multivariate logistic regression model together with other univariate predictors, the only independent determinants of critical illness polyneuropathy remained restrictive insulin schedule [or of 2.6 (1.6-4.2); P=0.0002], >3 days vasopressor treatment [or of 2.5 (1.4-4.2); P=0.001], acquiring a blood stream infection [or of 2.3 (1.3-4.1); P=0.006] and receiving renal replacement therapy [or of 1.9 (1.0-3.8); P=0.05].

When the risk of critical illness polyneuropathy was evaluated in both study groups as function of the actual mean glycemia per patient, a positive, linear correlation was obtained.

The amount of red cell transfusions in IIS patients was only half that of RIS patients. This was not due to a more liberal transfusion strategy in RIS patients as indicated by their lower levels of hemoglobin and hematocrit.

The cumulative TISS score is an indicator of the number of therapeutic interventions per patient and per ICU stay. There was a 20% reduction in median cumulative TISS score selectively in long-stay patients. In view of a comparable TISS score on the last day of study [median of 30 (26-38) in both study groups], this difference reflects a 20% reduction in costs per long-stay ICU patient.

In this large prospective, randomized, controlled study of intensive care-dependent critically ill patients, tight glycemic control below 6.1 mmol/L with insulin reduced ICU mortality by 43% and in-hospital mortality by 34%. Strict metabolic control also substantially improved morbidity by preventing blood stream infections, renal failure, anemia, critical illness polyneuropathy and need for prolonged support of failing vital organ systems. These striking benefits were independent of the type and severity of underlying disease.

The beneficial effects on morbidity can be summarized as reducing the risk of several key problems in intensive care. These include acquiring severe infections and ensuing inflammatory response, development of renal failure, cholestasis, anemia, critical illness polyneuropathy and muscle weakness. These problems perpetuate the need for intensive care which, in view of the high mortality of prolonged critical illness, often becomes futile.

In conclusion, the data suggest that disturbances in glucose metabolism in critically ill patients are not "adaptive and beneficial" since strict glycemic control during intensive care substantially reduces morbidity and mortality.

Use of Intravascular Equilibrium Sensor to Achieve Glycemic Control

The Van Den Berghe data and conclusions described above, as well as earlier publications from Furnary and colleagues (see e.g., Zerr et al., Ann Thorac Surg 1997 63:356-361), suggest that tight glycemic control may significantly reduce complications, shorten ICU stays, and improve outcome. Unfortunately, despite the significant benefits, it is still considered acceptable clinical ICU practice to allow blood glucose levels to increase as high as to 250 mg/dL or above before intervention. The reasons that medical and ICU personnel are disinclined to try to tightly regulate blood glucose in critically ill patients, e.g., within preferred target concentrations of about 80 to 110 mg/dl, are several fold. First, some practitioners believe that high levels of blood glucose may be part of the adaptive stress responses and that low blood glucose levels during stress is potentially deleterious for the immune system and for healing (Mizock B A. Am J Med 1995; 98: 75-84). As a practical matter, without continuous glucose monitoring and a reliable indication of the rate and direction (rising or falling) of changes in blood glucose concentration following insulin administration, ICU staff are inclined to err on the side of tolerating relative hyperglycemia rather than risk acute hypoglycemia induced by insulin. In view of the foregoing, Applicants have postulated that the clinical benefits of tight glycemic control in the critically ill ICU patient may be facilitated and enhanced by use of an intravascular glucose sensor capable of accurate continuous glucose monitoring, and wherein the sensor is operably coupled to a monitor in which the rate and direction of the change in blood glucose may be displayed. The sensor calibration methods disclosed herein play a role in allowing these intravascular glucose sensors to measure glucose concentration and/or glucose activity with sufficient accuracy to be relied up by ICU staff making critical medical decisions. Furthermore, the one-point calibration methods described above (typically preceded by a factor calibration) are convenient enough that ICU staff are not deterred from taking the time to properly calibrate these glucose sensors.

Thus, in accordance with a preferred embodiment, a method is disclosed for achieving glycemic control in a patient in need thereof, preferably in a patient under care in an intensive care unit, wherein the glycemic control is sufficient to reduce the incidence and/or severity of at least one critical illness polyneuropathy or other complication. The method comprises deploying an equilibrium glucose sensor within a blood vessel in the patient; operably coupling the sensor to a monitor that displays the blood glucose concentration and the rate and direction of changes in blood glucose concentration, and optionally generates an alarm signal when the blood glucose concentration and/or rate and direction of change varies outside of a predetermined range; and administering a blood glucose regulator when the blood glucose concentration varies outside of the predetermined range, wherein the blood glucose regulator is administered in an amount sufficient to return the blood glucose concentration to within the predetermined concentration range and/or reverse a rising or falling trend, thereby achieving glycemic control. The predetermined concentration range may be from about 60 to about 180 mg/dl glucose, more preferably from about 60 to about 130 mg/dl glucose, and yet more preferably from about 80 to about 110 mg/dl. The blood glucose regulator may be glucose or insulin or insulin analogs or derivatives, or other hypoglycemic agents, or any known agents or combinations that regulate blood glucose.

Figure 19A:
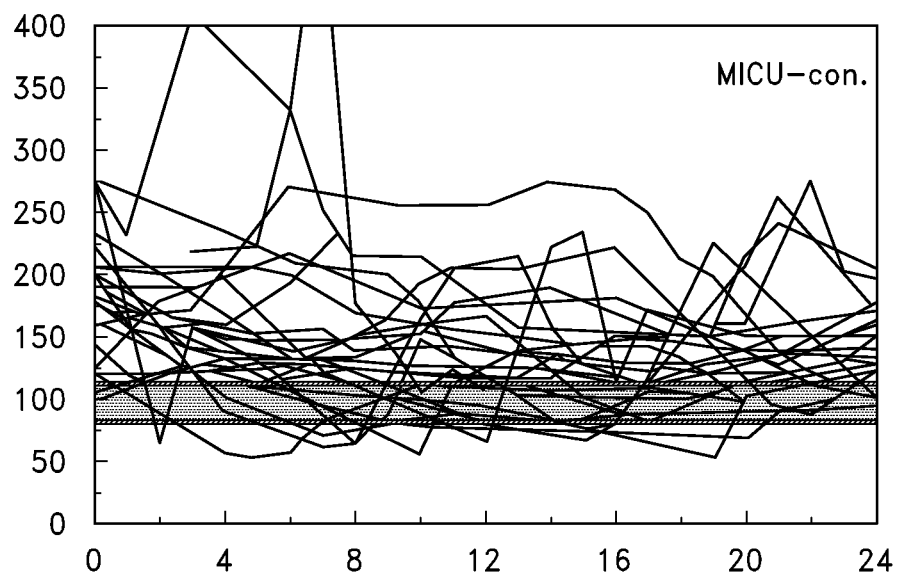
FIG. 19A illustrates typical blood glucose concentrations in medical ICU patients.
Figure 19B:
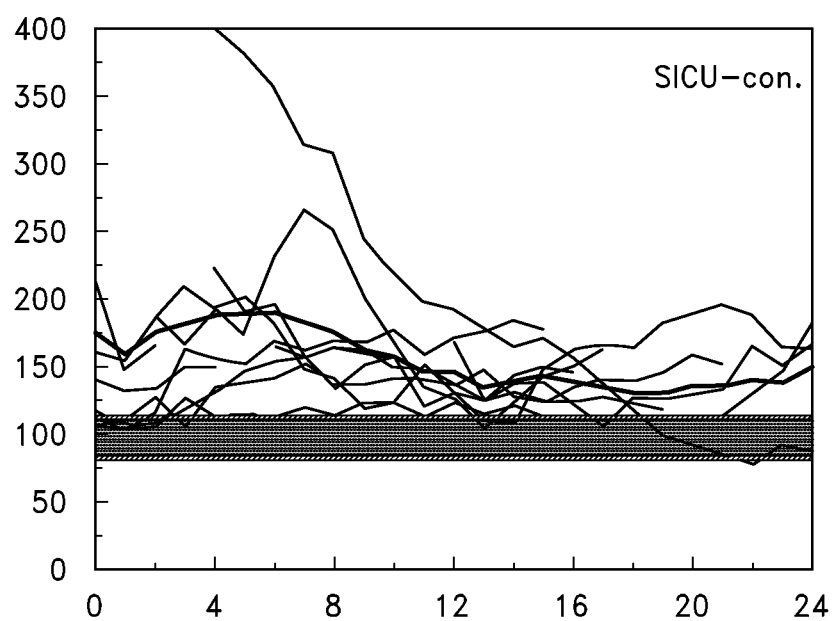
FIG. 19B illustrates typical blood glucose concentrations in surgical ICU patients.

With reference to FIGS. 19A and 19B, typical blood glucose concentrations in medical ICU and surgical ICU are shown; these data are from Mader et al., Diabetes Technology Meeting, San Francisco, Calif. (2007). The shaded bar indicates the target blood glucose range (80-110 mg/dl). The thicker line represents the calculated average, and the many lines are from individual patients. Clearly, there is a great challenge in trying to achieve tight glycemic control in these patient populations, in which the blood glucose varies tremendously over time.

Figures 20A, 20B:
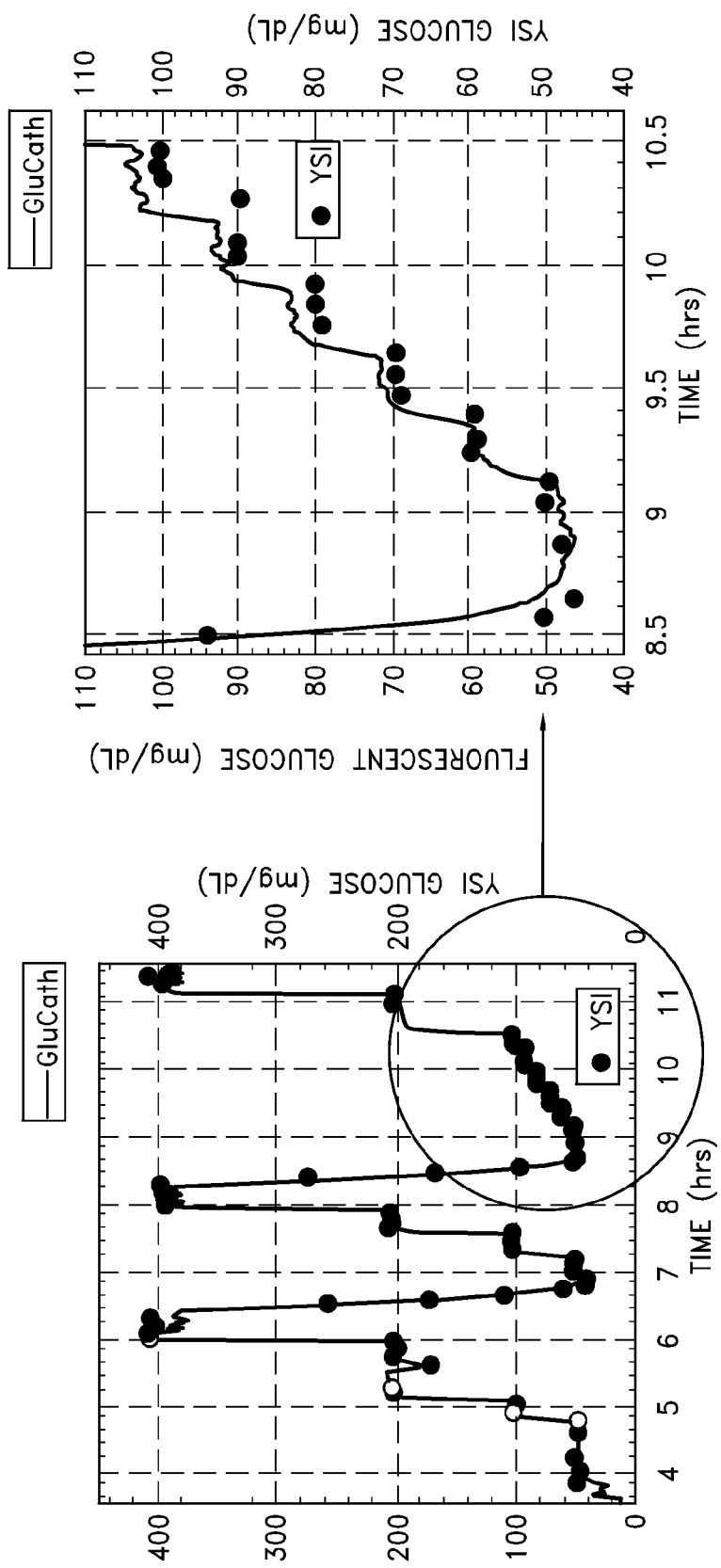
FIGS. 20A and 20B compare the results of glucose readings taken over time with the GluCath sensor and with the Yellow Springs Instrument glucose oxidase lab analyzer.

With reference to FIGS. 20A and 20B, the results of glucose determination over time and with infused glucose in a circulating blood loop in vitro are compared for a continuous glucose sensor in accordance with one preferred embodiment (-GluCath) and the Yellow Springs Instrument glucose oxidase lab analyzer (●YSI), the gold standard of blood glucose measurements. The GluCath equilibrium fluorescence glucose sensor used in this experiment comprised HPTS-tri-CysMA dye and 3,3'-oBBV quencher. FIG. 20A shows an 8 hr time course with changes in circulating glucose in the range of 50-400 mg/dl. FIG. 20B is an expanded illustration of the two hr stepwise addition of 10 mg/dl boluses. The data show that the equilibrium fluorescence glucose sensor provides continuous monitoring of blood glucose which is as accurate as the YSI lab analyzer. The expanded view in FIG. 20B shows rapid and accurate sensing even at very low levels of blood glucose (between 50 and 100 mg/dl). This is surprising since accurate detection in such a low range has been extremely difficult to accomplish with other detection devices. The lack of accurate and reliable blood glucose sensing below 100 mg/dl has hampered ICU attempts to maintain target blood glucose levels, because of the significant clinical risk of going too low.

Figure 21A:
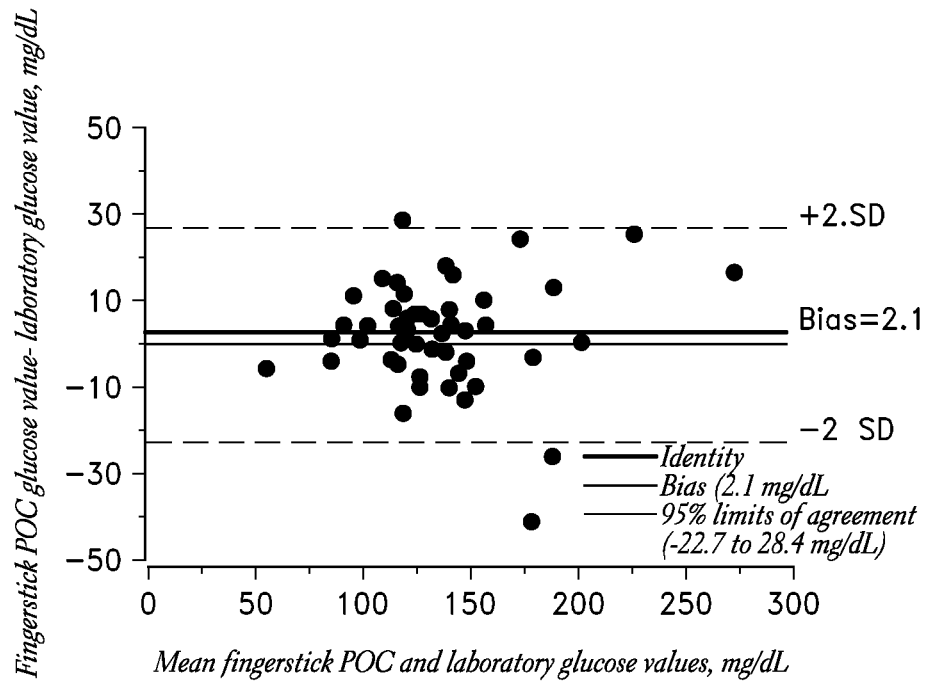
FIG. 21A displays an Bland-Altman plot showing the differences between laboratory references and fingerstick POC for in vivo blood glucose monitoring.
Figure 21B:
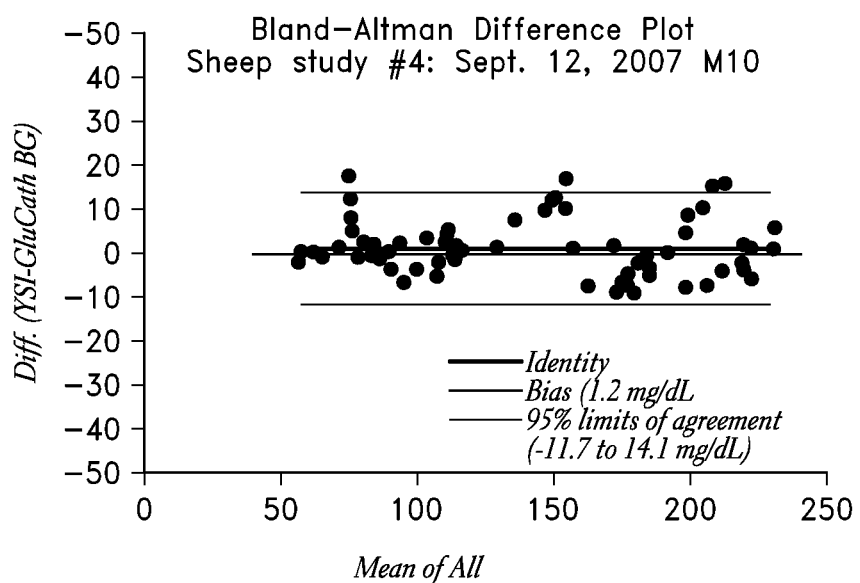
FIG. 21B displays an Bland-Altman plot showing the differences between laboratory references and a GluCath indwelling equilibrium fluorescence glucose sensor for in vivo blood glucose monitoring.

With reference to FIGS. 21A and 21B, Bland-Altman plots show differences between laboratory references and either fingerstick POC (FIG. 21A) or GluCath indwelling equilibrium fluorescence glucose sensor (FIG. 21B) for in vivo blood glucose monitoring. FIG. 21A shows results of blood glucose detection using a standard fingerstick test compared to a clinical chemistry system. The 95% confidence limits vary from −22.7 to 28.4 mg/dl with a bias of 2.1 mg/dl. It is noteworthy that very few readings below 100 mg/dl can be seen. FIG. 21B shows results of blood glucose detection using GluCath continuous equilibrium fluorescence glucose sensor, deployed intravascularly in sheep compared to the YSI lab analyzer. The differences are much tighter, with 95% confidence limits of −11.7 to 14.1 mg/dl and a bias of only 1.2 mg/dl. There are many more data points below 100 mg/dl.

Example 1

A 65 year old male is admitted to an intensive care unit following open heart surgery. After he is settled, a GluCath optical fiber sensor is deployed intravascularly. The sensor comprises an HPTS-tri-CysMA dye operably coupled to a 3,3'-oBBV quencher, immobilized within a hydrogel disposed along the distal region of the optical fiber sensor. The proximal end of the sensor is coupled to a light source and a programmable monitor adapted to display continuous real-time glucose concentration as well as rates and directions of changes in blood glucose levels. The monitor is programmed to generate an alarm when the blood glucose falls outside of the target range (below 80 mg/dl or above 110 mg/dl). Continuous readout of the rate and direction of blood glucose trend and blood glucose concentration allows ICU staff to determine whether intervention is needed. As soon as the sensor goes on-line, the blood glucose concentration reads out on the monitor at 300 mg/dl and is rising. An ICU nurse administers insulin at a dose calculated to reduce the blood glucose level to within the target range. Within a few minutes the blood glucose begins to drop. The physician is concerned that the glucose will drop too fast and overshoot the target low concentration of 80 mg/dl. Within two hours, the blood glucose concentration is at 100 mg/dl and is steady. After several hours of routine care, the blood glucose concentration begins to rise. When the glucose concentration goes above 110 mg/dl, the alarm on the monitor alerts the ICU staff to the rising glucose level. An ICU nurse administers an amount of insulin sufficient to reduce the blood glucose to within the programmed range. The ICU staff is able to maintain control of the patient's blood glucose concentration during the next 7 days in the ICU. The recovery is smooth and no critical illness polyneuropathy or other complications are observed.

Example 2

A glucose sensor comprising a fluorescent based sensing system was evaluated in an 8-hour outpatient feasibility study approved by an Institutional Review Board. The glucose sensor was placed in a peripheral vein at the antecubital fossa in five subjects with type 1 diabetes. Sensor insertion was performed using a 22 Ga needle and a retractable cannula. One sensor was damaged during the insertion process and failed to produce any useful data.

Data from the other four sensors were taken at one-minute intervals and compared with hospital and laboratory blood glucose measurements from venous samples in the contralateral arm every 15 minutes. Data was analyzed retrospectively using a temperature-corrected factory calibration with a one-point in vivo adjustment made within thirty minutes of the sensor insertion. The glucose sensor results were compared with measurements made on a Radiometer ABL 805 Flex blood gas analyzer (BGA), a Yellow Springs Instrument (YSI) analyzer 2300 StatPlus and the LifeScan SureStep Flexx Pro.

Figure 22:
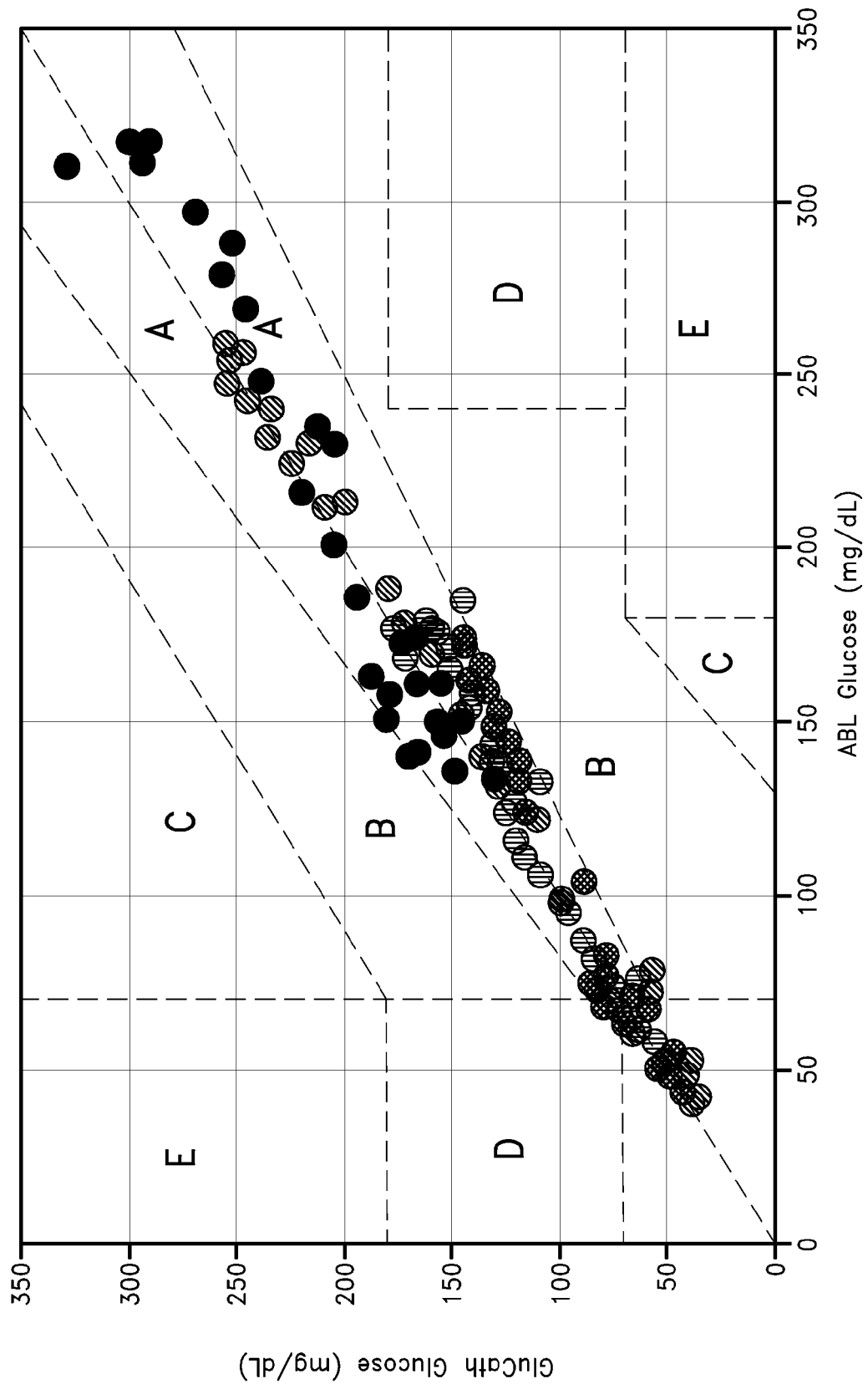
FIG. 22 displays a Clerke error grid showing the differences between laboratory references.
Figure 23:
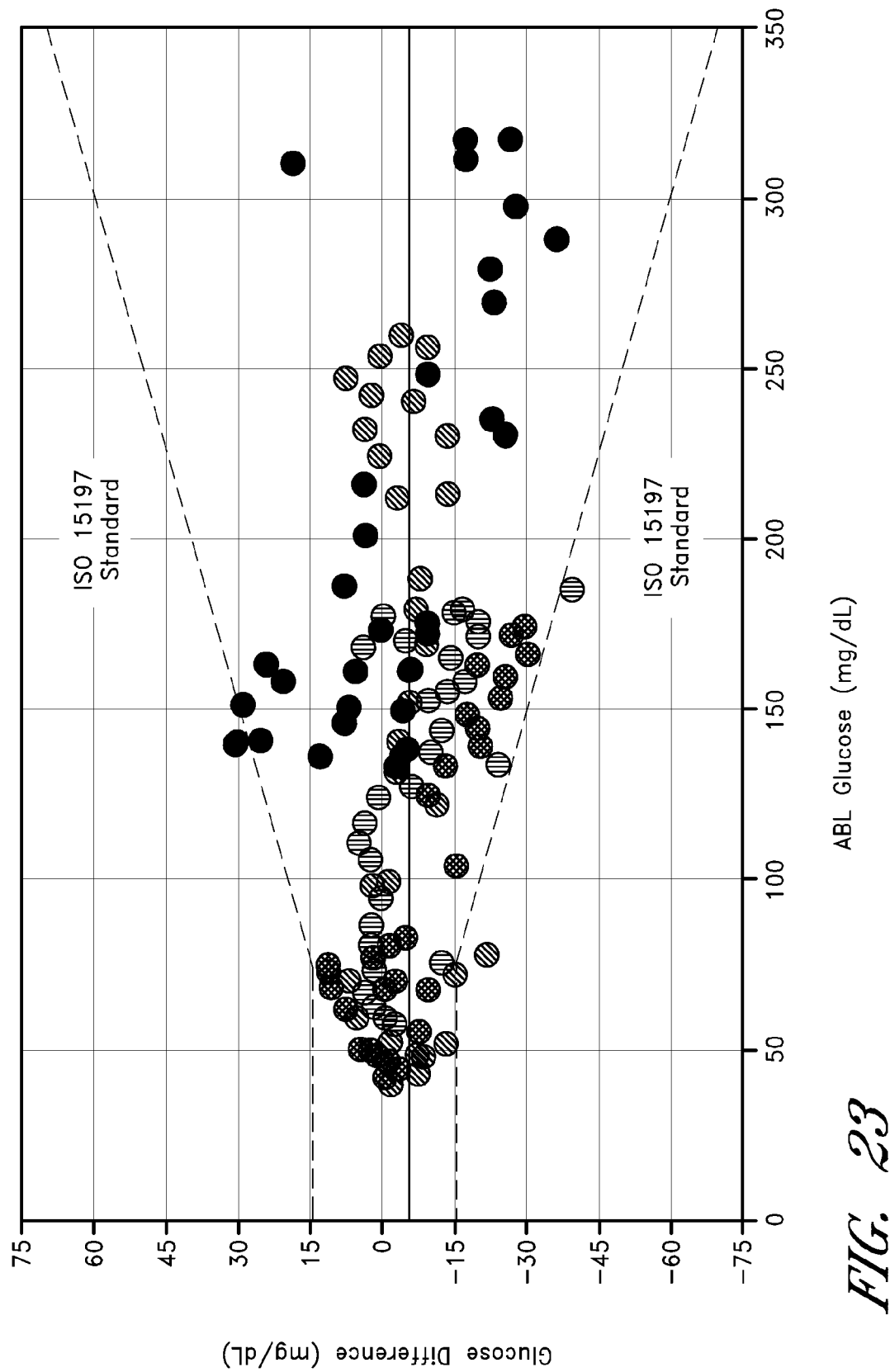
FIG. 23 displays an Bland-Altman plot showing the differences between laboratory references.

The glucose sensor was found to be highly accurate compared with laboratory reference measurements (Radiometer ABL BGA), especially in the hypoglycemic range. Comparison of the GluCath results to the Radiometer ABL BGA values found the GluCath accuracy met the performance standard in ISO-15197: 100% (30/30) of all values ≤75 mg/dL were within ±15 mg/dL of the reference values, see Table 3A, and 96.8% (90/93) of all points >75 mg/dL were ±20% of the reference measurements, see Table 3B. The mean absolute relative difference (MARD) was 7.70%, see Table 4 and FIG. 22. The mean bias under an ISO-15197 Bland-Altman plot was −5.50 mg/dL, see FIG. 23.

TABLE 3A

| Performance Data at ≤75 mg/dL | |
| --- | --- |
| ≤±5 mg/dL | 17/30 (56.7%) |
| ≤±10 mg/dL | 25/30 (83.3%) |
| ≤±15 mg/dL | 30/30 (100%) |

TABLE 3B

| Performance Data at >75 mg/dL | |
| --- | --- |
| ≤±5% | 42/93 (45.2%) |
| ≤±10% | 68/93 (73.1%) |
| ≤±15% | 80/93 (86.0%) |
| ≤±20% | 90/93 (96.8%) |

TABLE 4

Glucose Stratified Clarke & MARD

| Glucose (mg/dL) | # of samples | Clarke "A" Zone | MARD |
| --- | --- | --- | --- |
| ≤50 | 10 | 10/10 (100%) | 7.60% |
| 51-80 | 23 | 21/23 (91.3%) | 9.80% |
| 81-120 | 12 | 12/12 (100%) | 3.80% |
| 120-240 | 64 | 62/64 (96.9%) | 8.10% |
| ≥241 | 14 | 14/14 (100%) | 5.50% |
| ALL | 123 | 119/123 (96.7%) | 7.70% |

This is one of the first use in human subjects of a fluorescent glucose sensor. The sensor was found to be highly accurate compared with laboratory reference measurements, especially in the hypoglycemic range.

What is claimed is:

1. A method for determining glucose concentration in a physiologic fluid, the method comprising:
   providing an optical sensor comprising a non-enzymatic, equilibrium fluorescence chemical indicator system disposed along a distal region of an optical fiber, the chemical indicator system comprising a fluorophore operably coupled to a glucose binding moiety, wherein the fluorophore is configured to generate a fluorescent emission signal upon excitation with light, and wherein glucose binding to the glucose binding moiety causes a change in the fluorescent emission signal related to the glucose concentration in the physiologic fluid;
   contacting the chemical indicator system with the physiologic fluid;
   exciting the fluorophore with light, thereby generating a fluorescent emission signal related to the glucose concentration in the physiologic fluid;
   detecting the intensity of the fluorescent emission signal;
   obtaining a value of the fluorescent emission signal intensity in the absence of glucose;
   obtaining a value of the asymptotic intensity of the fluorescent emission signal at infinite glucose;
   obtaining a value of the glucose concentration at which the fluorescent emission intensity is one-half the difference between the fluorescent emission signal intensity in the absence of glucose and the asymptotic intensity of the fluorescent emission signal at infinite glucose; and
   processing the fluorescent emission signal intensity by transforming the fluorescent emission signal intensity into a glucose concentration value using the equation:

$[G]=c*(I-a)/(a+b-I)$, wherein

[G] is the glucose concentration,
   I is the fluorescent emission signal intensity,
   a is the value of the fluorescent emission signal intensity in the absence of glucose,
   b is the value of the asymptotic signal intensity at infinite glucose concentration, minus the fluorescent signal intensity in the absence of glucose (a), and
   c is the value of the glucose concentration at which the fluorescent signal intensity is one-half the difference between the asymptotic value (b) and the background (a).

2. The method of claim 1, wherein a, b and c are determined from a set of ex vivo measurements of the fluorescent emission signal(s) generated using one or more solutions of known glucose concentrations.

3. The method of claim 2, wherein a, b and c are determined during a factory calibration of the chemical indicator system.

4. The method of claim 3, further comprising an ex vivo calibration of the optical sensor using one or more solutions of known glucose concentration to determine a correction factor.

5. The method of claim 4, further comprising an in vivo or in vitro calibration with an independent glucose measurement.

6. The method of claim 4, wherein the ex vivo calibration comprises:
   measuring a first fluorescent emission signal generated in the presence of a known glucose concentration at a first temperature and time; and
   measuring a second fluorescent emission signal generated in the presence of the same known glucose concentration at a second temperature and time.

7. The method of claim 4, wherein the ex vivo calibration comprises:
   measuring a first fluorescent emission signal generated in the presence of a known glucose concentration of 0 mg/dL, and
   measuring a second fluorescent emission signal generated in the presence of a known glucose concentration of 100 mg/dL, and
   measuring a third fluorescent emission signal generated in the presence of a known glucose concentration of 400 mg/dL.

8. The method of claim 1, further comprising:
   measuring the fluorescent emission signal after contacting the chemical indicator system with the physiologic fluid,
   measuring the glucose concentration in the physiologic fluid by a method independent of the chemical indicator system,
   calculating a correction factor by comparing the measured fluorescent emission signal with a predicted signal calculated by the glucose concentration measured independently of the chemical indicator system; and
   correcting a, b and c with the correction factor.

9. The method of claim 1, wherein the physiologic solution is blood.

10. The method of claim 1, wherein the optical sensor includes a mirror and a thermistor each placed at the distal end of the optical fiber, wherein the method further comprises sensing the temperature at the thermistor, and wherein the exciting the fluorophore with light includes reflecting the light off of the mirror into the optical fiber.

* * * * *